United States Patent
Schlaepfer et al.

(10) Patent No.: US 10,758,277 B2
(45) Date of Patent: Sep. 1, 2020

(54) BONE FIXATION ASSEMBLY

(71) Applicant: DePuy Synthes Products, Inc., Raynham, MA (US)

(72) Inventors: Fridolin Schlaepfer, Hoelstein (CH); Martin Schnider, Subingen (CH); Helmut Rutschmann, Klettgau (DE)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/682,213

(22) Filed: Aug. 21, 2017

(65) Prior Publication Data
US 2017/0340360 A1    Nov. 30, 2017

Related U.S. Application Data

(63) Continuation of application No. 14/081,117, filed on Nov. 15, 2013, now Pat. No. 9,763,702.

(60) Provisional application No. 61/731,772, filed on Nov. 30, 2012, provisional application No. 61/727,290, filed on Nov. 16, 2012.

(51) Int. Cl.
*A61B 17/70*    (2006.01)

(52) U.S. Cl.
CPC ........ *A61B 17/704* (2013.01); *A61B 17/7037* (2013.01); *F04C 2270/0421* (2013.01); *Y10T 29/49826* (2015.01)

(58) Field of Classification Search
CPC ..................................... A61B 17/70–17/7098
See application file for complete search history.

(56) References Cited

U.S. PATENT DOCUMENTS

| 3,865,105 A | 2/1975 | Lode |
| 4,411,259 A | 10/1983 | Drummond |
| 5,219,349 A | 6/1993 | Krag et al. |

(Continued)

FOREIGN PATENT DOCUMENTS

| AU | 727020 | 11/2000 |
| CA | 2275952 | 10/2006 |

(Continued)

OTHER PUBLICATIONS

Expedium® 5.5 Titanium Spine System, product catalog, DePuy Spine, Inc., 2013, 34 pages.

(Continued)

*Primary Examiner* — Nicholas J Plionis
(74) *Attorney, Agent, or Firm* — Meunier Carlin & Curfman LLC

(57) ABSTRACT

An anchor assembly for use in spinal fixation to interconnect a longitudinal spinal rod with a patient's vertebra. The anchor assembly preferably includes a bone anchor, a body with a rod-receiving channel, an insert member (preferably a bushing), and a locking cap. The anchor assembly enables in-situ assembly where the bone anchor may be secured to the patient's vertebra prior to being received within the body of the bone anchor assembly. Accordingly, the anchor assembly enables a surgeon to implant the bone anchor without the body to maximize visibility and access around the anchoring site. Once the bone anchor has been secured to the patient's vertebra, the body may be snapped onto the bone anchor and a spinal rod may be inserted into the rod-receiving channel.

20 Claims, 27 Drawing Sheets

(56) References Cited

U.S. PATENT DOCUMENTS

| | | | |
|---|---|---|---|
| 5,281,223 A | 1/1994 | Ray | |
| 5,385,565 A | 1/1995 | Ray | |
| 5,478,340 A | 12/1995 | Kluger | |
| 5,490,851 A | 2/1996 | Nenov et al. | |
| 5,632,744 A | 5/1997 | Campbell, Jr. | |
| 5,672,175 A | 9/1997 | Martin | |
| 5,800,434 A | 9/1998 | Campbell, Jr. | |
| 5,814,046 A | 9/1998 | Hopf | |
| 6,067,262 A | 6/2000 | Schläpfer et al. | |
| 6,090,113 A | 7/2000 | Couedic et al. | |
| 6,224,598 B1 | 5/2001 | Jackson | |
| 6,258,090 B1 | 7/2001 | Jackson | |
| 6,361,535 B2 | 3/2002 | Jackson | |
| 6,379,356 B1 | 4/2002 | Jackson | |
| 6,551,316 B1 | 4/2003 | Rinner et al. | |
| 6,726,687 B2 | 4/2004 | Jackson | |
| 6,726,692 B2 | 4/2004 | Bette | |
| 6,730,089 B2 | 5/2004 | Jackson | |
| 6,746,449 B2 | 6/2004 | Jones et al. | |
| 6,755,828 B2 | 6/2004 | Shevtsov et al. | |
| 7,004,947 B2 | 2/2006 | Shluzas et al. | |
| 7,188,626 B2 | 3/2007 | Foley et al. | |
| 7,278,995 B2 | 10/2007 | Nichols et al. | |
| 7,572,281 B2 | 8/2009 | Runco et al. | |
| 7,611,517 B2 | 11/2009 | Lim | |
| 7,618,444 B2 | 11/2009 | Shluzas | |
| 7,625,376 B2 | 12/2009 | Brumfield et al. | |
| 7,655,008 B2 | 2/2010 | Lenke et al. | |
| 7,658,753 B2 | 2/2010 | Carl et al. | |
| 7,670,358 B2 | 3/2010 | Barry | |
| 7,686,814 B2 | 3/2010 | Lim et al. | |
| 7,708,765 B2 | 5/2010 | Carl et al. | |
| 7,722,617 B2 | 5/2010 | Young et al. | |
| 7,744,598 B2 | 6/2010 | Brumfield et al. | |
| 7,758,584 B2 | 7/2010 | Bankoski et al. | |
| 7,776,072 B2 | 8/2010 | Barry | |
| 7,776,074 B2 | 8/2010 | Bray | |
| 7,794,464 B2 | 9/2010 | Bridwell et al. | |
| 7,799,031 B2 | 9/2010 | Miller et al. | |
| 7,811,288 B2 | 10/2010 | Jones et al. | |
| 7,824,411 B2 | 11/2010 | Varienr et al. | |
| 7,951,168 B2 | 5/2011 | Chao et al. | |
| 7,951,175 B2 | 5/2011 | Chao et al. | |
| 8,002,801 B2 | 8/2011 | Carl et al. | |
| 8,007,516 B2 | 8/2011 | Chao et al. | |
| 8,016,860 B2 | 9/2011 | Carl et al. | |
| 8,043,333 B2 | 10/2011 | Frigg et al. | |
| 8,394,133 B2 | 3/2013 | Jackson | |
| 8,900,272 B2 | 12/2014 | Jackson | |
| 9,144,444 B2 | 9/2015 | Jackson | |
| 2005/0245928 A1 | 11/2005 | Colleran et al. | |
| 2006/0122597 A1 | 6/2006 | Jones et al. | |
| 2006/0200131 A1* | 9/2006 | Chao | A61B 17/7037 606/278 |
| 2006/0271050 A1 | 11/2006 | Vallespir | |
| 2007/0118123 A1* | 5/2007 | Strausbaugh | A61B 17/7038 606/272 |
| 2007/0288004 A1 | 12/2007 | Alvarez | |
| 2008/0004629 A1 | 1/2008 | Nichols et al. | |
| 2008/0154277 A1 | 6/2008 | Machalk et al. | |
| 2008/0221626 A1 | 9/2008 | Butters et al. | |
| 2008/0294206 A1 | 11/2008 | Choi et al. | |
| 2009/0012567 A1* | 1/2009 | Biedermann | A61B 17/7032 606/264 |
| 2009/0204159 A1 | 8/2009 | Justis et al. | |
| 2009/0216237 A1 | 8/2009 | Frezal et al. | |
| 2009/0228051 A1 | 9/2009 | Kolb et al. | |
| 2009/0228054 A1 | 9/2009 | Hoffman et al. | |
| 2009/0228055 A1 | 9/2009 | Jackson | |
| 2009/0259262 A1 | 10/2009 | Nayet | |
| 2009/0281582 A1 | 11/2009 | Villa et al. | |
| 2010/0004695 A1 | 1/2010 | Stad et al. | |
| 2010/0030283 A1 | 2/2010 | King et al. | |
| 2010/0069972 A1 | 3/2010 | Jones et al. | |
| 2010/0121385 A1 | 5/2010 | Blain et al. | |
| 2010/0121386 A1 | 5/2010 | Peultier et al. | |
| 2010/0152787 A1 | 6/2010 | Walsh et al. | |
| 2010/0185242 A1 | 7/2010 | Barry et al. | |
| 2010/0185248 A1 | 7/2010 | Barry et al. | |
| 2010/0198272 A1* | 8/2010 | Keyer | A61B 17/7037 606/302 |
| 2010/0228302 A1 | 9/2010 | Danster et al. | |
| 2010/0234902 A1 | 9/2010 | Biedermann et al. | |
| 2010/0280560 A1 | 11/2010 | Brumfield et al. | |
| 2010/0318129 A1 | 12/2010 | Seme et al. | |
| 2012/0010661 A1 | 1/2012 | Farris et al. | |
| 2012/0035670 A1 | 2/2012 | Jackson et al. | |
| 2012/0095516 A1* | 4/2012 | Dikeman | A61B 17/7032 606/305 |
| 2012/0136395 A1 | 5/2012 | Biedermann et al. | |
| 2012/0143265 A1* | 6/2012 | Biedermann | A61B 17/7032 606/328 |
| 2012/0209336 A1 | 8/2012 | Jackson et al. | |
| 2013/0096622 A1* | 4/2013 | Biedermann | A61B 17/70 606/279 |
| 2013/0110172 A1* | 5/2013 | Biedermann | A61B 17/7035 606/278 |
| 2014/0094849 A1* | 4/2014 | Spratt | A61B 17/7035 606/257 |
| 2014/0277159 A1* | 9/2014 | Spratt | A61B 17/7037 606/278 |

FOREIGN PATENT DOCUMENTS

| | | |
|---|---|---|
| DE | 69723108 | 4/2004 |
| EP | 528177 | 9/1996 |
| EP | 553782 | 4/1997 |
| EP | 955930 | 6/2003 |
| EP | 1374786 | 2/2004 |
| EP | 1392190 | 8/2006 |
| JP | 10-248855 A | 9/1998 |
| JP | 2000/350731 | 12/2000 |
| WO | 2012/091737 | 7/2012 |

OTHER PUBLICATIONS

Expedium Spine System: DI Independent Locking Technology, product brochure, DePuy Spine, Inc., 2004, 6 pages.

Expedium Spine System: Dual-Innie Screw, product specification sheet, DePuy Spine, Inc. 2011, 2 pages.

Examination Notice, dated Nov. 30, 2016, received in connection with corresponding EP Patent Application No. 13193245.1.

Examination Notice, dated Apr. 28, 2016, received in connection with corresponding EP Patent Application No. 13193245.1.

Examination Notice, dated Apr. 27, 2015, received in connection with corresponding EP Patent Application No. 13193245.1.

Extended European Search Report, dated Feb. 17, 2014, received in connection with European Patent Application No. 13193245.1.

* cited by examiner

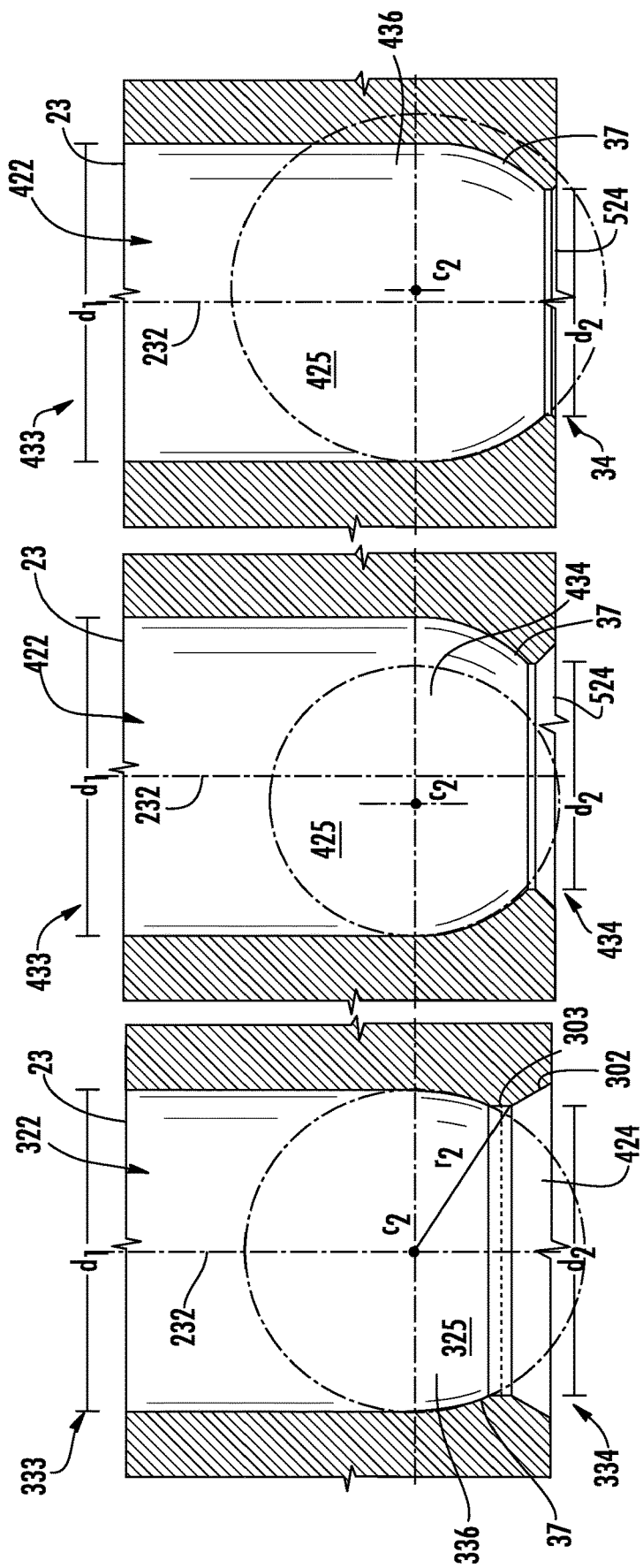

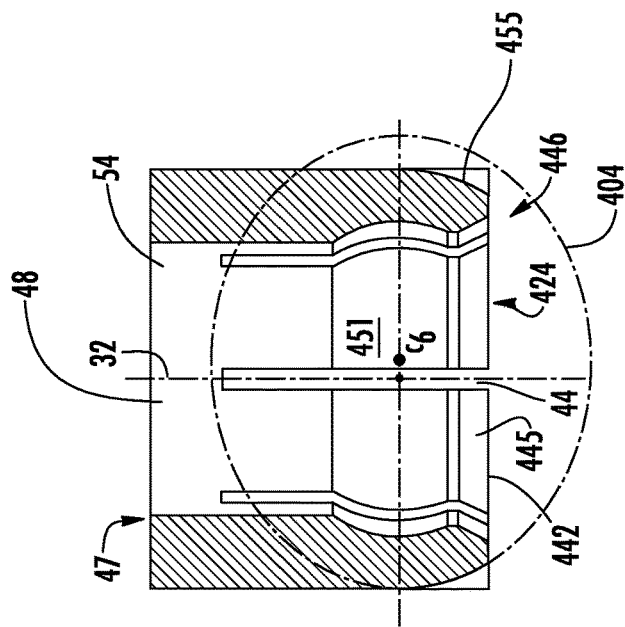
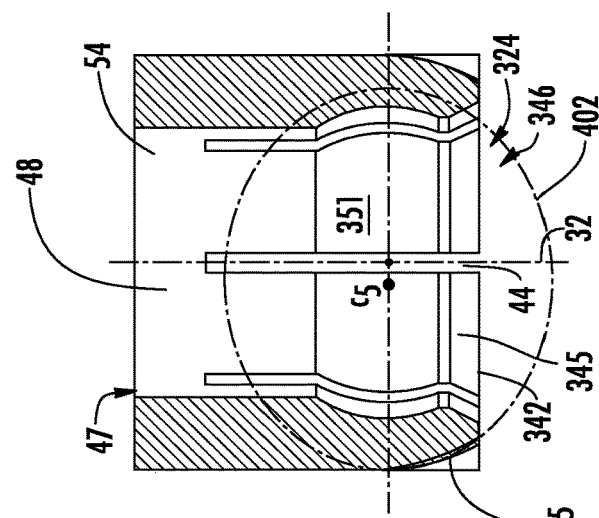
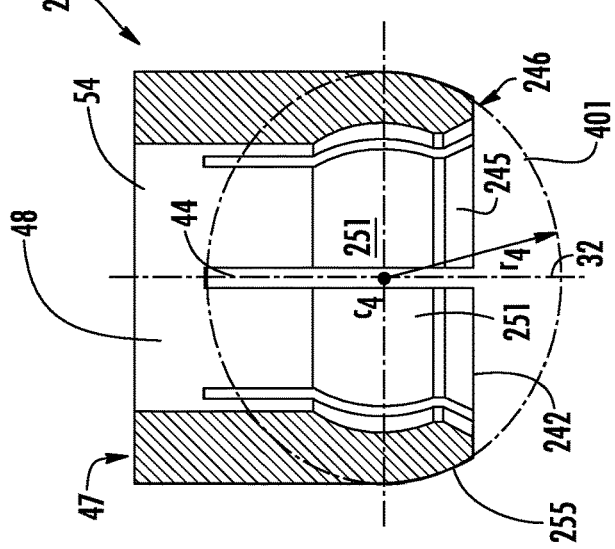

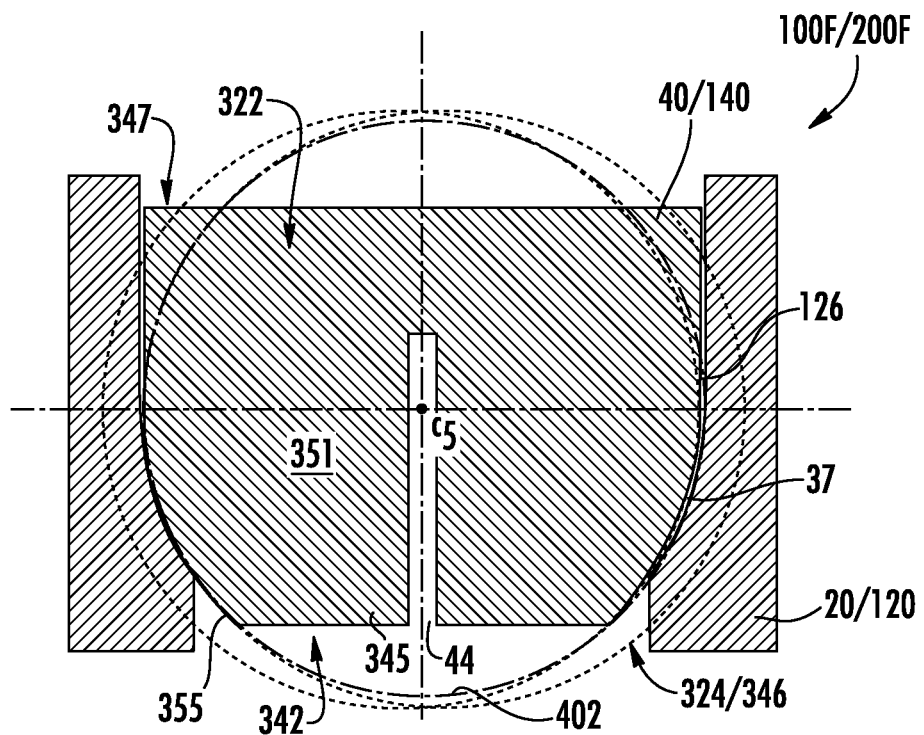
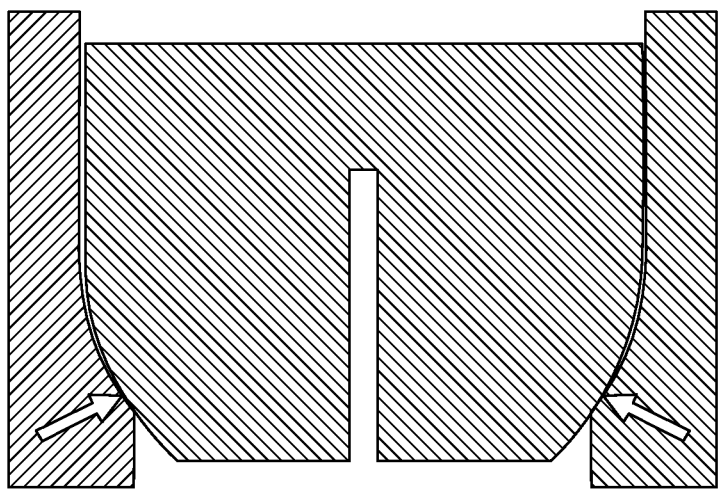
FIG. 10A
FIG. 10B

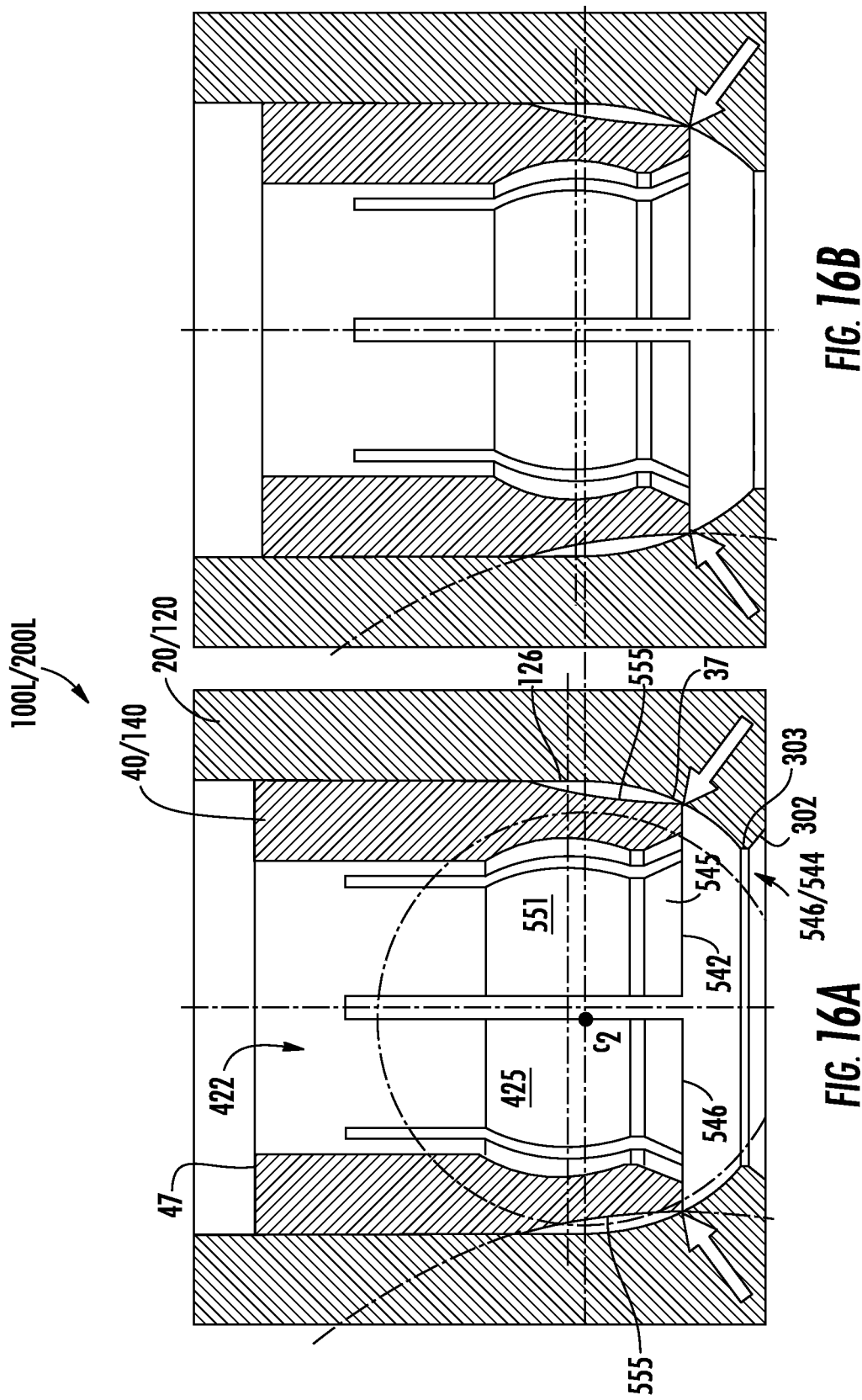

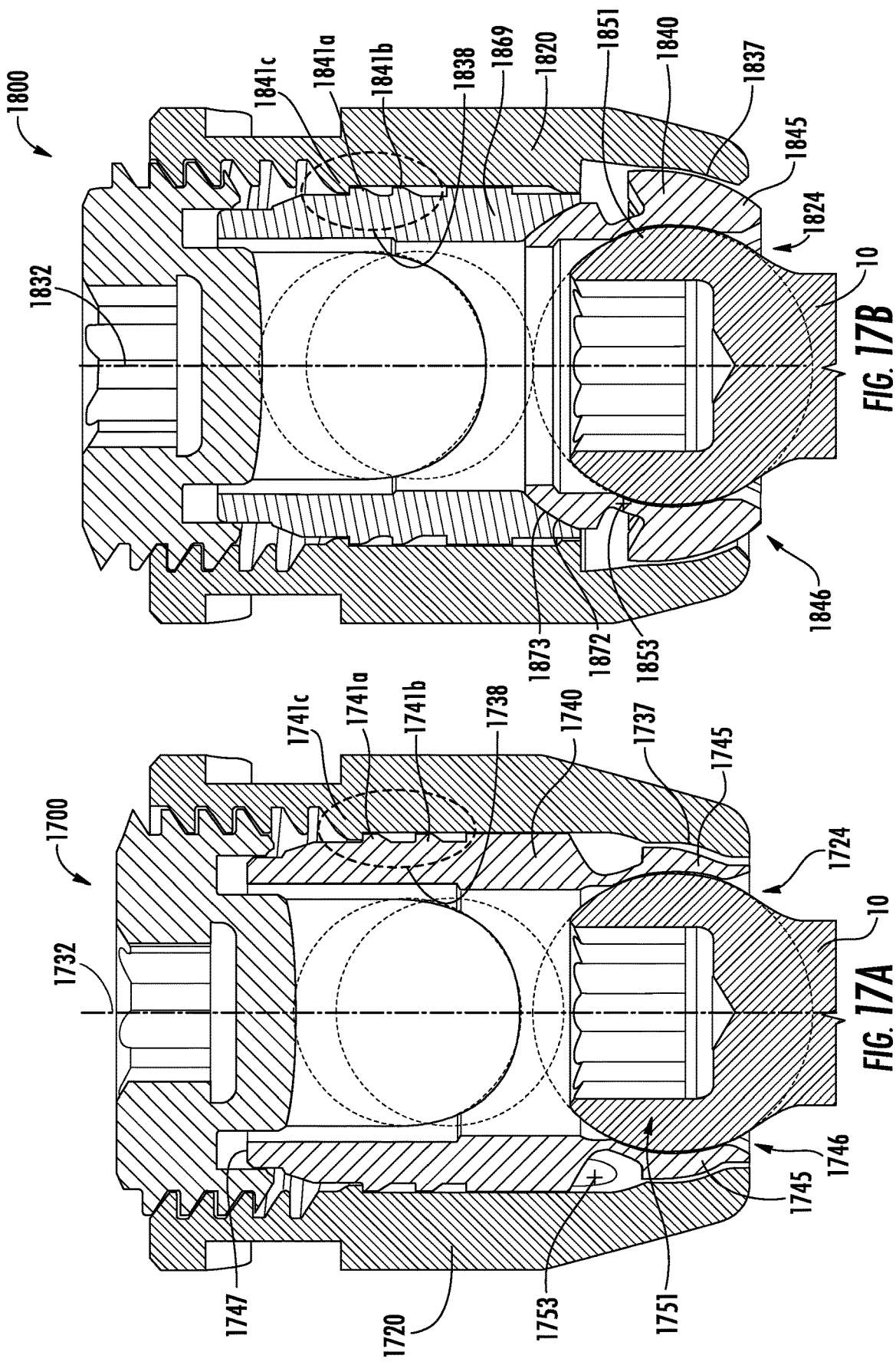

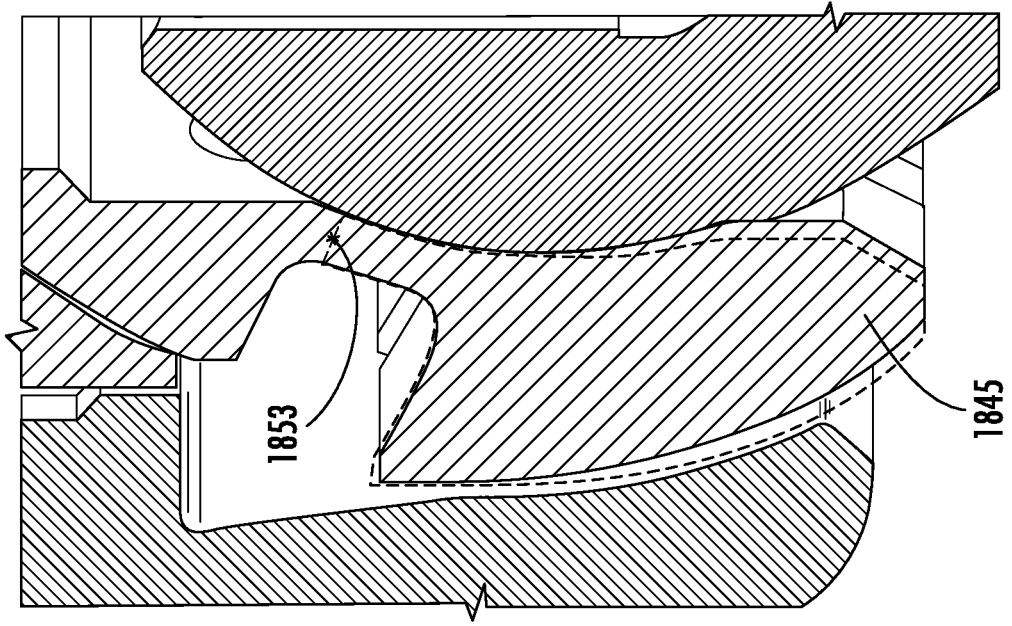
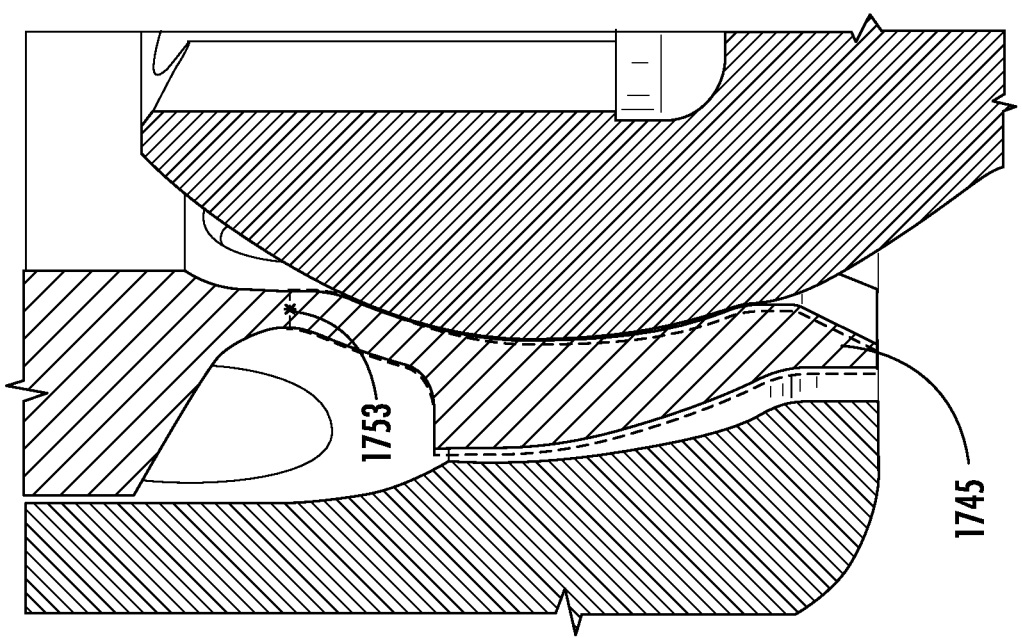

BONE FIXATION ASSEMBLY

CROSS-REFERENCE TO RELATED APPLICATIONS

This application is a continuation of U.S. patent application Ser. No. 14/081,117, filed Nov. 15, 2013, titled "Bone Fixation Assembly," which claims the benefit of provisional U.S. Patent Application No. 61/727,290, filed Nov. 16, 2012, titled "Bone Fixation Assembly," and provisional U.S. Patent Application No. 61/731,772, filed Nov. 30, 2012, titled "Reduction Tool for Use with Bone Fixation Assembly," the contents of which are hereby incorporated by reference.

BACKGROUND

As a result of various spinal disorders, it often is necessary to surgically correct and stabilize spinal curvatures, or to facilitate spinal fusion. Numerous systems for treating spinal disorders have been developed. For example, one example includes a bone fixation system that has a pair of elongated members, typically spinal rods, longitudinally placed on the posterior spine on either or both sides of the spinous processes of the vertebral column. Each rod is attached to various vertebrae along the length of the spine by way of bone fixation or bone anchor assemblies, e.g., pedicle screws. The body of the pedicle screw often has a rod-receiving channel and receives a locking cap to secure the spinal rod to the pedicle screw. To facilitate insertion of the spinal rod into the rod-receiving channels of the pedicle screws, pedicle screws have been developed wherein the body is separate from and pivotable with respect to the bone anchor (commonly known as polyaxial pedicle screws).

SUMMARY

The present disclosure relates generally to orthopedics. In more particularity, the present disclosure is directed to a bone anchor assembly for use in a spinal fixation procedure that connects a support member (e.g., a spinal rod) to a vertebra. The anchor assembly preferably includes a bone anchor having a head portion (e.g., a bone screw), an insert member (e.g., a bushing), a body having a bore for receiving the insert member and a rod receiving channel, and a locking cap engageable with the body and for receiving the spinal rod. The bone anchor assembly preferably enables in-situ assembly. That is, the anchor assembly may be configured so that in use, the bone anchor may be secured to the patient's vertebra prior to being connected to the body. Accordingly, the anchor assembly preferably enables a surgeon to implant the bone anchor without the body and bushing to maximize visibility and access around the anchoring site. Once the bone anchor has been secured to the patient's vertebra, the body can "click-on" to the bone anchor.

In some implementations, the anchor assembly includes bone anchor moveable with respect to a body subassembly prior to fixing the position of the spinal support member to the body subassembly. The body subassembly may be sized and configured to snap onto the head of the bone anchor and may include an insert member (e.g., a bushing), and receives a locking cap. The head portion preferably may include a first tool interface for engaging a first surgical instrument operatively associated with the bone anchor. The body preferably includes a longitudinal axis, an interior wall, an upper end with an upper opening, a lower end with a lower opening, a bore extending between the upper opening and the lower opening, and a rod-receiving channel. The rod-receiving channel may be configured and arranged to receive a spinal rod.

The bushing may include an upper end and a lower portion that captures, and at least partially surrounds, the head portion of the bone anchor. The lower portion of the bushing includes at least one, preferably a plurality of, slot(s) extending from the lower end, the slots preferably defining a plurality of flexible arms, wherein each of the flexible arms have an outer surface. The bushing may be movably positionable within the bore of the body.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The foregoing summary, as well as the following detailed description of preferred embodiments of the disclosure, will be better understood when read in conjunction with the appended drawings. The preferred embodiments of a bone anchor system including a bone anchor assembly are shown in the drawings for the purposes of illustration. It should be understood, however, that the application is not limited to the precise arrangements, structures, features, embodiments, instrumentalities, and methods shown and described, and the arrangements, structures, features, embodiments, instrumentalities, and methods shown and described may be used singularly or in combination with other arrangements, structures, features, embodiments, instrumentalities, and methods. In the drawings:

FIGS. 3A-3E illustrate various configurations of a body of the bone anchor assembly;

FIGS. 4A-4D illustrate various configurations of a bushing of the bone anchor assembly;

FIGS. 10A-10B illustrate a front sectional view of a sixth embodiment of a polyaxial pedicle screw assembly of the present disclosure;

FIGS. 16A-16B illustrate a front sectional view of an eleventh embodiment of a polyaxial pedicle screw assembly of the present disclosure;

FIGS. 17A and 18A illustrate a third embodiment of bone anchor or bone fixation assembly; and FIGS. 17B and 18B is illustrated a fourth embodiment of bone anchor or bone fixation assembly.

DETAILED DESCRIPTION

Figure 1A:
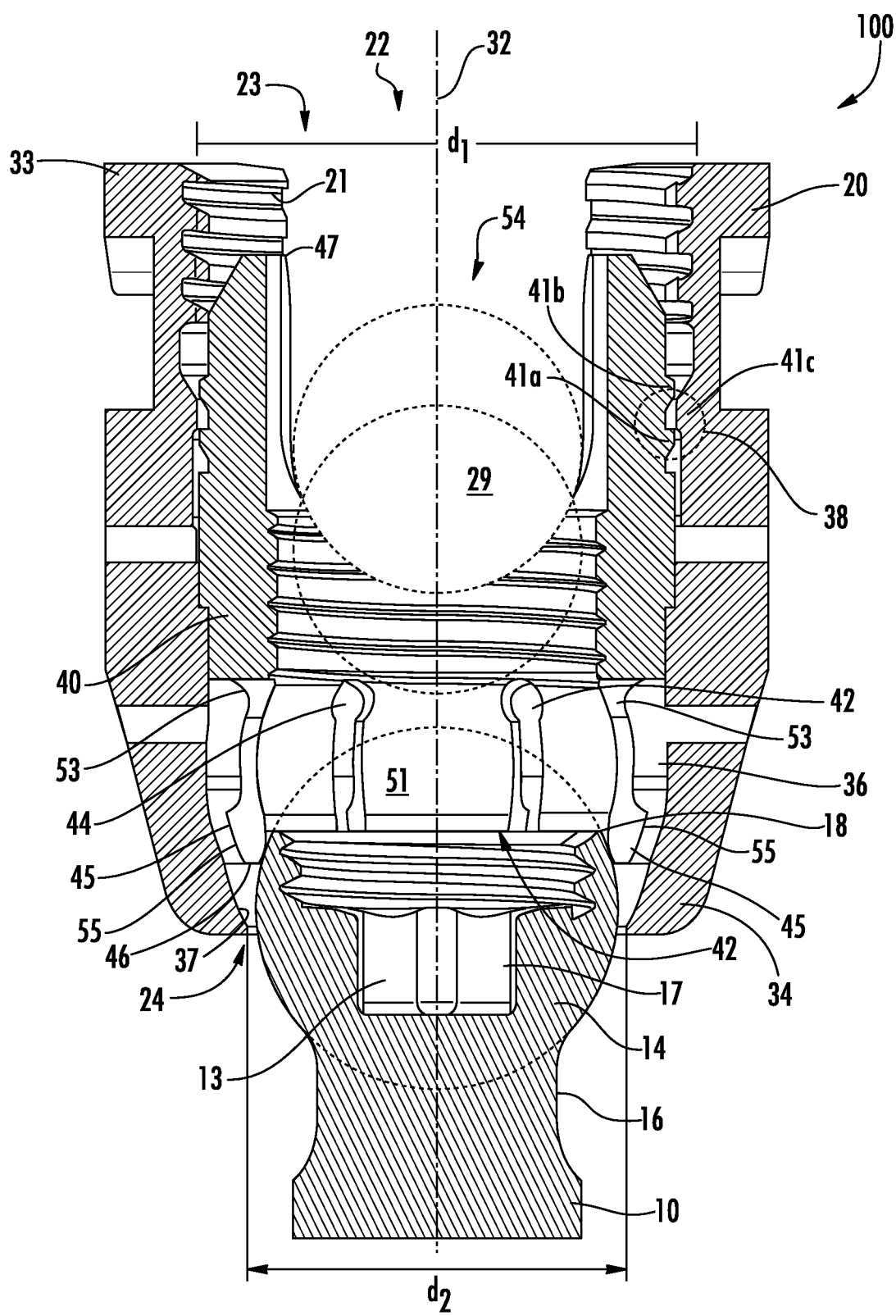
FIGS. 1A-1D illustrate a side perspective view of a first embodiment of a bone anchor assembly in accordance with the present disclosure.
Figure 1B:
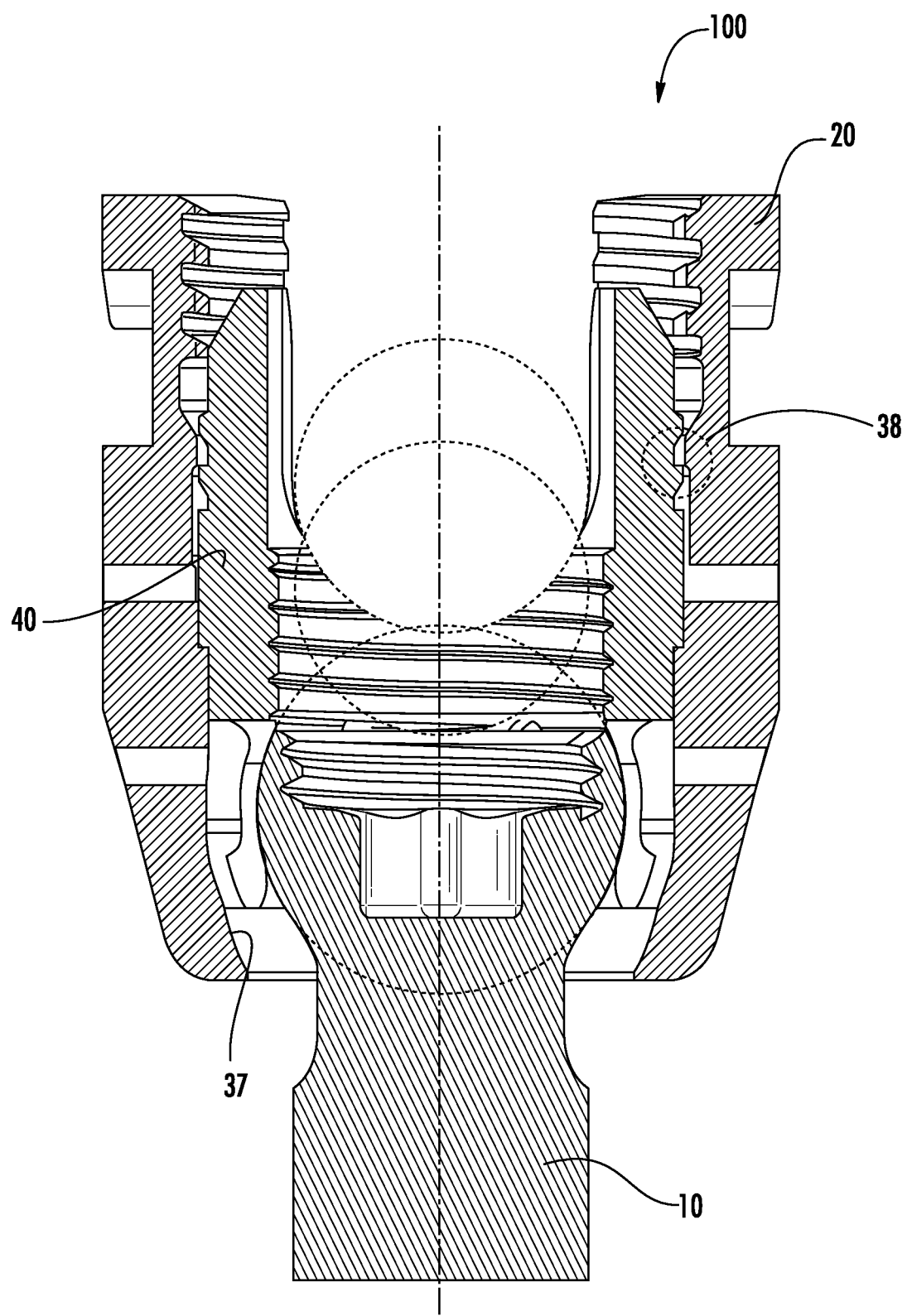

Certain terminology is used in the following description for convenience only and is not limiting. The words "right", "left", "lower", "upper", "below", "above", "top", and "bottom" designate directions in the drawings to which reference is made. The words "inwardly" or "distally" and "outwardly" or "proximally" refer to directions toward and away from, respectively, the geometric center of the bone anchor system and/or assembly, the described instruments and designated parts thereof. The words, "anterior", "posterior", "superior", "inferior", "medial", and "lateral" and related words and/or phrases designate preferred positions and orientations in the human body to which reference is made and are not meant to be limiting. The terminology includes the above-listed words, derivatives thereof and words of similar import.

Certain exemplary implementations of the disclosure will now be described with reference to the drawings. In general, such implementations relate to a polyaxial bone fixation element
threaded ring 60 and set screw 90 may be supplied and assembled during the surgical implantation of the bone fixation assembly 100.

Figure 1C:
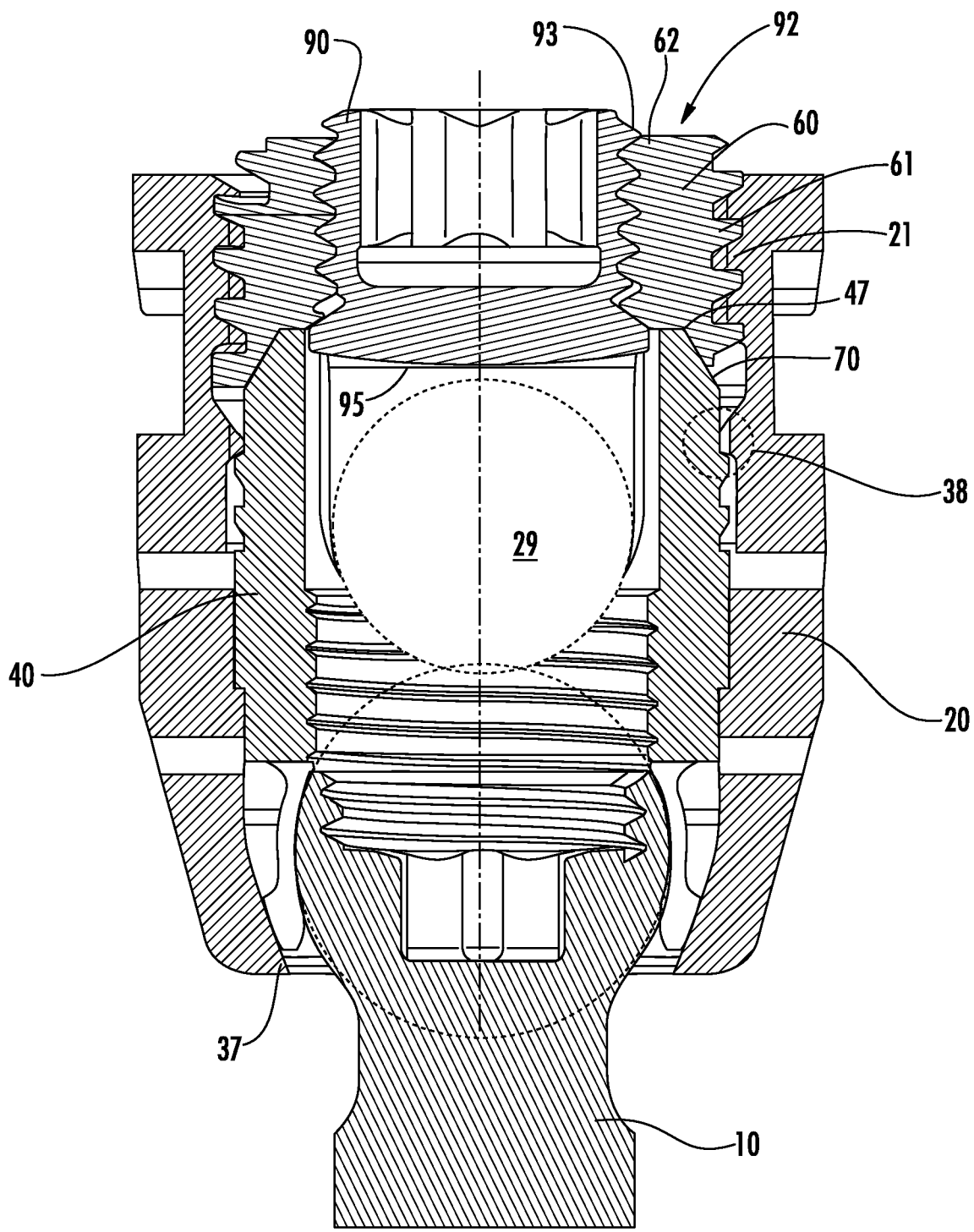
Figure 1D:
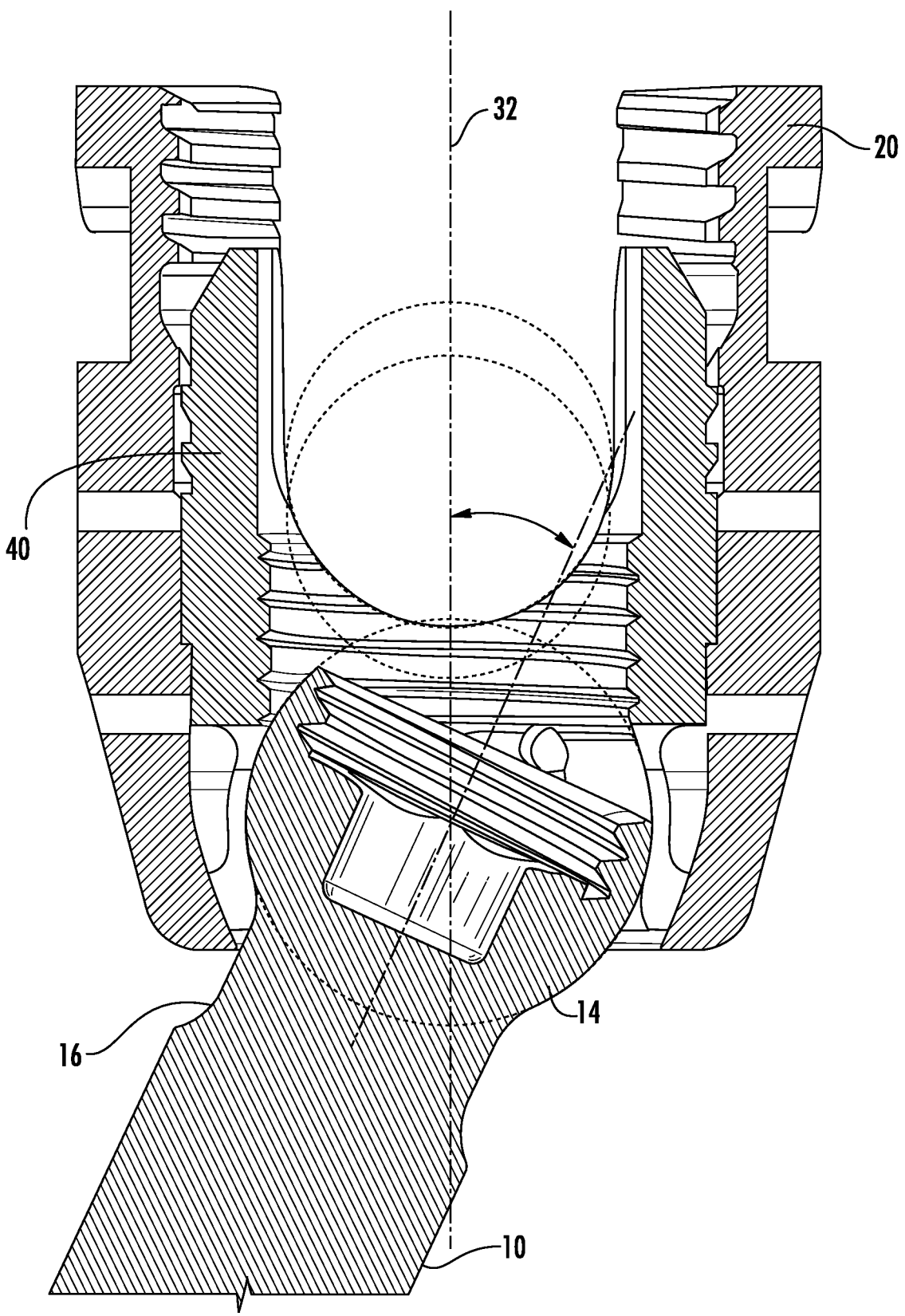

With reference to FIG. 1C, to lock the bone anchor 10 once the rod is placed into the rod receiving channel 29, the locking cap 92 may be placed into the upper opening 23 of the body 20. The threaded ring 60 may then be threadably engaged with the threads 21 of the body 20 to connect the locking cap 92 to the body 20. By engaging the locking cap 92 with the body 20, the rod-receiving channel 29 is closed and the spinal rod is captured and retained in the bone fixation assembly 100. To lock the movement of the spinal rod and the bone anchor 10 with respect to the body 20, the threaded ring 60 is tightened and moves downward in the body 20. As the threaded ring 60 is moved further downward in the body 20, the threaded ring 60 pushes down on the upper end 47 and angled section 70 which pushes down on bushing 40, causing the arms 45 of the bushing 40 to further collapse around the head 14 of the bone anchor 10, thereby securing the bushing 40 in the locked position, thus securing the position of the bone anchor 10 with respect to the body 20. As such, the threaded ring 60 controls the locking of the bone anchor 10.

In accordance with the above, to lock the rod in place, the setscrew 90 is tightened and as the setscrew 90 moves down within the bore of the threaded ring 60, the bottom surface 95 of the setscrew 90 pushes down on the rod, thereby securing the position of the rod. This configuration provides the benefit of the anchor assembly 100 having a low profile when assembled.

The bone fixation assembly 100 may be provided to a user in a kit including (1) bone anchors, (2) locking caps, (3) pre-assembled bushing body subassemblies, bushing/sleeve/body subassemblies, or fastener element body subassemblies, and (4) spinal rods. The pre-assembled bushing body subassemblies, bushing/sleeve/body subassemblies or fastener element/body subassemblies may be assembled during manufacture by inserting the bushing 40 into the axial bore 22 formed in the body 20 through the upper opening 23 formed in the body 20 until the bushing 40 is captured and retained in the body. The kit may be delivered to the user for use in, e.g., spinal surgery. During surgery, the surgeon may identify a level of the spine where the surgery will take place, makes an incision to expose the selected area and implants one or more bone anchors into the desired vertebrae. The subassembly may be clicked-on to the bone anchor 10 by urging the head 14 through the lower opening 24 in the body 20. Accordingly, the body subassembly may be engaged with the head 14 of the bone anchor 10 in situ. The anchor assembly including the bone anchor 10, the bushing 40, the body 20, and the locking cap 92 may be made from any biocompatible material including, but not limited to, metals such as, for example, titanium, titanium alloys, stainless steel, cobalt chromium, Nitinol, etc. Other materials such as, for example, composites, polymers, ceramics, and any other material may be used for the anchor assembly, its component parts, and spinal rods.

Referring to FIGS. 2A-2D, there is illustrated a second implementation of a bone anchor or bone fixation assembly 200 that generally includes a bone anchor 10 (e.g., a bone screw), a body 120, a bushing 140, and a locking cap 92. The elements of the second implementation that are the same as the first implementation of FIGS. 1A-1D will not be described again below. The body 120 may generally be described as a cylindrical tubular body having a rod receiving channel 129, a longitudinal axis 132, an upper end 133 having an upper opening 123, a lower end 134 having a lower opening 124, and an axial bore 122 substantially coaxial with the longitudinal axis 132 of the body 120. The axial bore 122 extends from the upper opening 123 to the lower opening 124 and has a lower chamber 136 having ledges 149.

The axial bore 122 at the upper opening 123 has a first diameter d11 and, at the lower opening 24, has a second diameter d12, which may be smaller than the first diameter d11. The second diameter d12 may be sized and configured so that the head 14 of the bone anchor 10 may be passed through the lower opening 124 of the body 120. An inner surface of the axial bore 122 includes a plurality of threads 121 in the upper end for engaging the locking cap 92. The body 120 and the axial bore 122 may have nearly any mounting structure for engaging the locking cap 192 including, but not limited to, external threads, cam-lock, quarter lock, clamps, lugs, bayonets, etc.

Figure 2A:
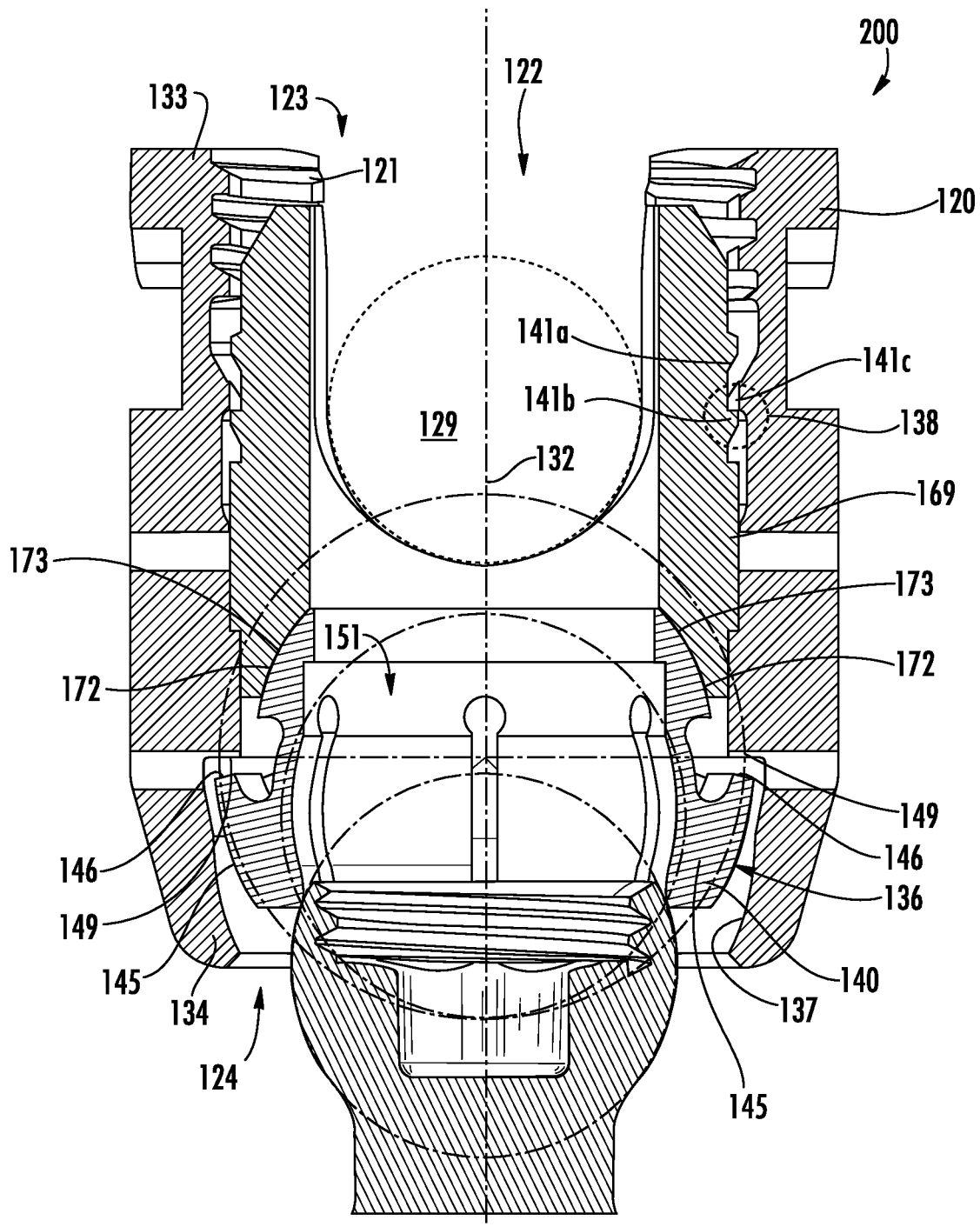
FIGS. 2A-2F illustrate a side perspective view of a second embodiment of a bone anchor assembly in accordance with the present disclosure.
Figure 2B:
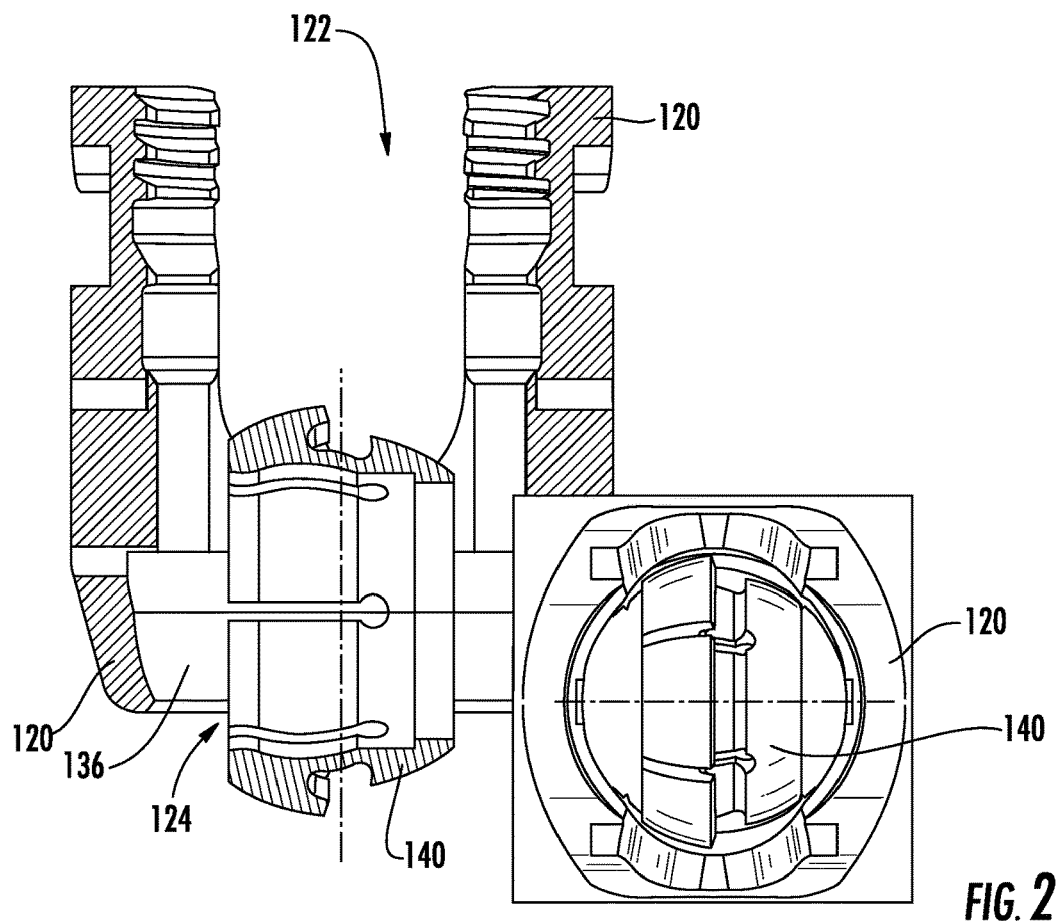
Figure 2C:
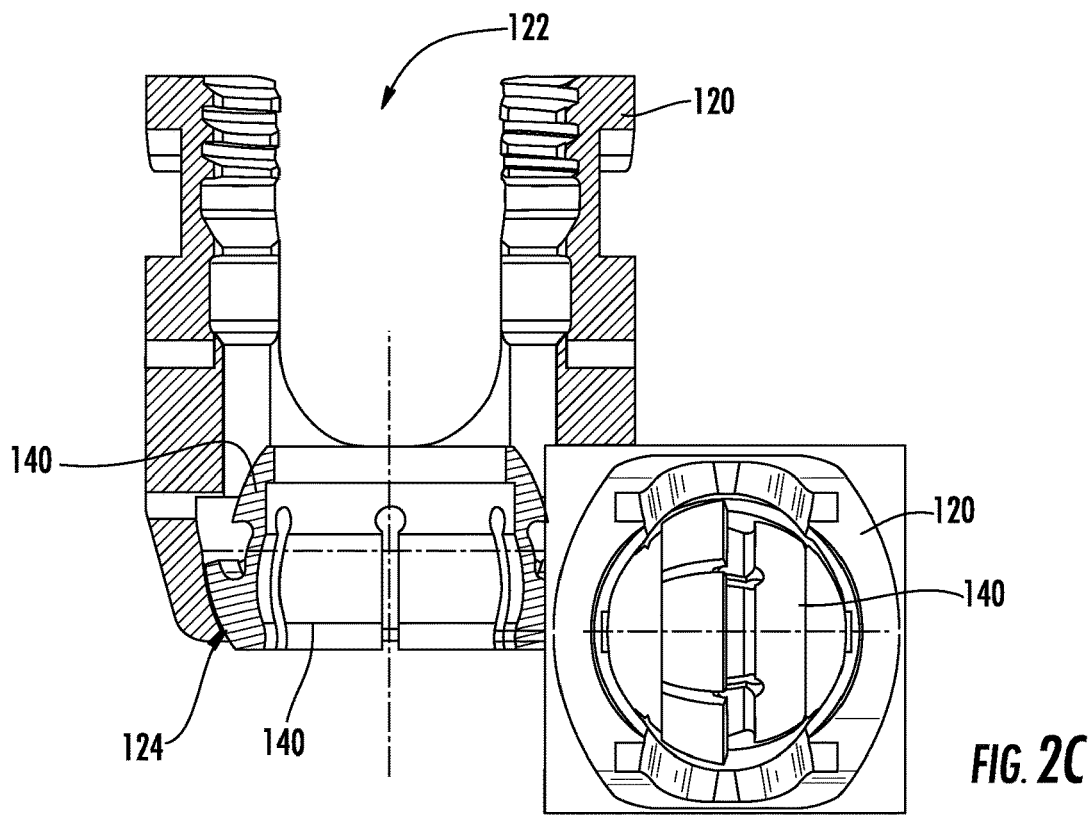

As shown in FIG. 2B-2C, the bushing 140 is sized and configured such that it may be inserted into the body 120 through the upper opening 123, but is prevented from exiting through the lower opening 124. As shown in FIG. 2B, the bushing 140 may be inserted into the body 120 in a rotated state, e.g., such that a longitudinal axis of the bushing 140 is perpendicular to the longitudinal axis 132 of the body 120. Once a portion of the bushing 140 passes through the lower opening 124, the bushing may be rotated such that the longitudinal axis of the bushing 140 is co-axial with the longitudinal axis 132 of the body 120 and such that the bushing 140 is positioned within the lower chamber 136 of the body 120 (FIG. 2C).

To place and retain the bushing 140 in the body 20, the saddle 169 preferably may be provided with structures, features, geometry and a configuration that interacts and interfaces with structures, features and geometry of the body 120 and the bushing 140. In an example, the saddle 169 and body 20 may be provided with one or more ratchet teeth 141 as part of a locking mechanism 138 to prevent the bushing 140 from moving out of the body 120 through upper opening 123 and to lock the bushing 140 into a predetermined orientation within the body 120 when in the first (loading/unlocked) position (FIGS. 2A and 2D) and the second (loaded/locked) position (FIGS. 2E-2F).

Referring again to FIG. 2A, once the bushing 140 is placed and assembled into the body 120, the bushing 140 may be retained within the body 120 by a saddle 169 such that the bushing 140 is generally prevented from (1) passing back up through the upper opening 123 formed in the body 120; and (2) passing through the lower opening 124 formed in the body 120. For example, after the bushing 140 is rotated and positioned as shown in FIG. 2C, the saddle 169 may be inserted into the upper opening 123 such that a lower surface 173 of the saddle 169 contacts an upper surface 172 of the bushing 140. As such, the bushing 140 is retained within the lower chamber 136 of the body 120.

Figure 2D:
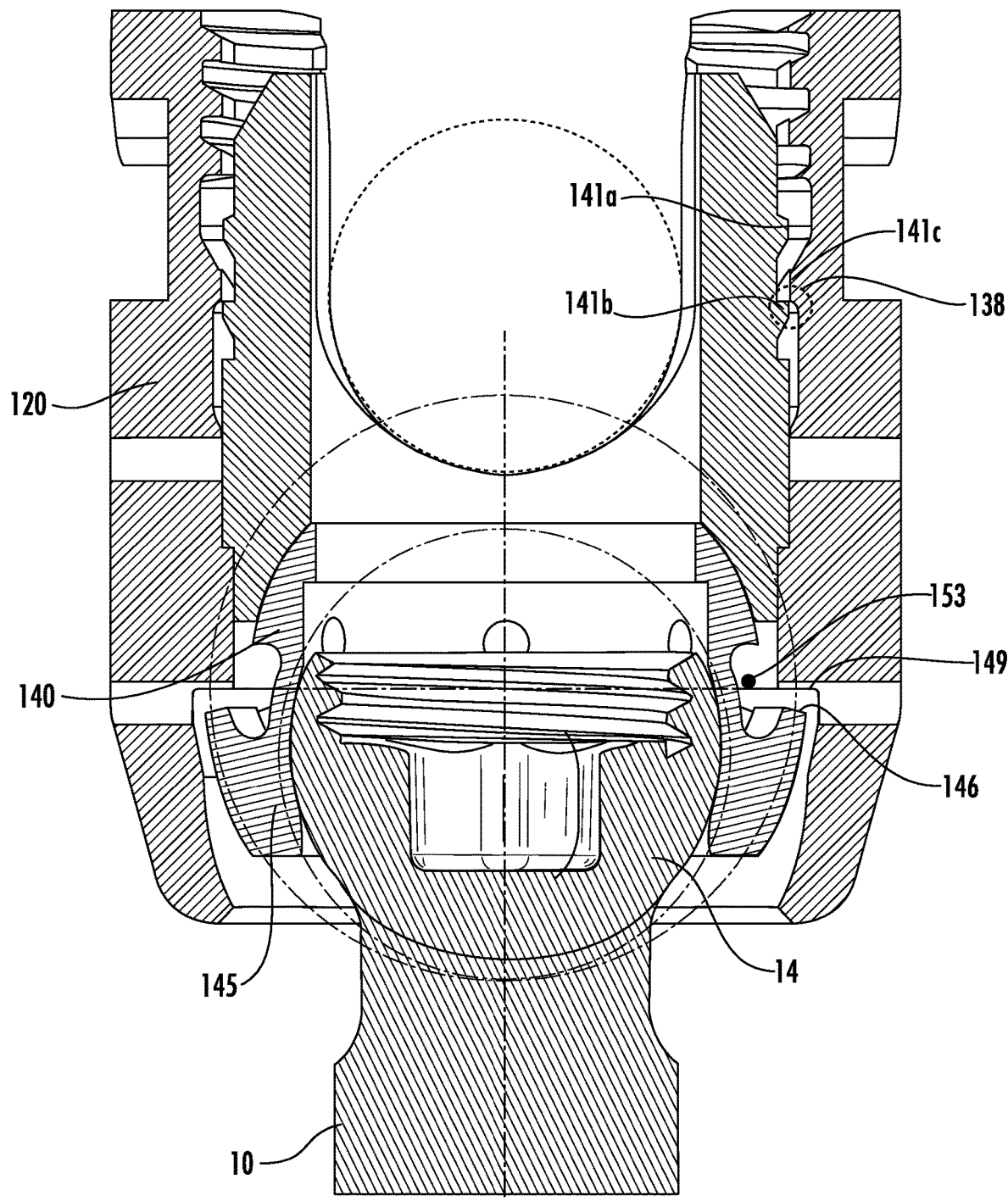
Figure 2E:
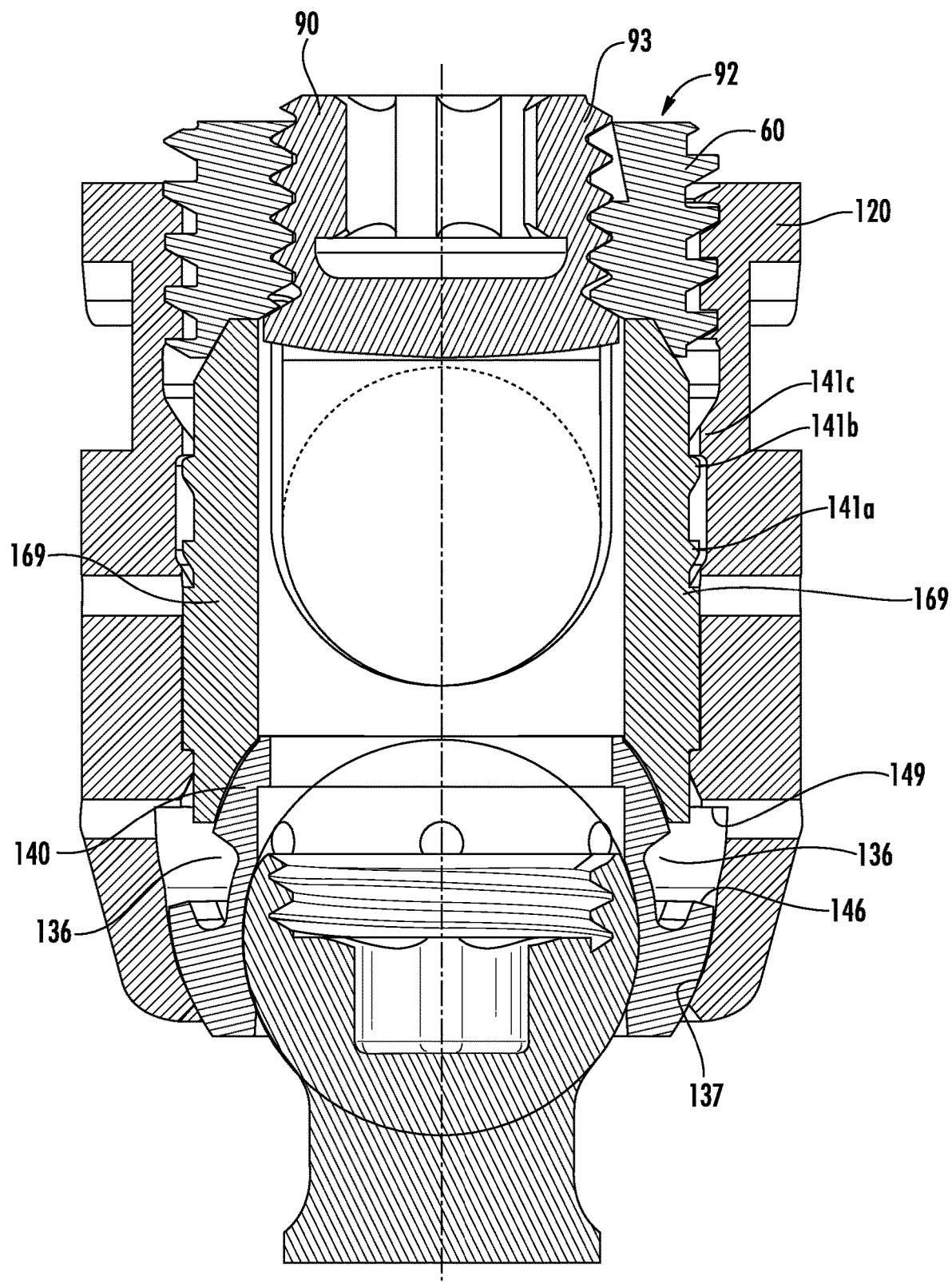
Figure 2F:
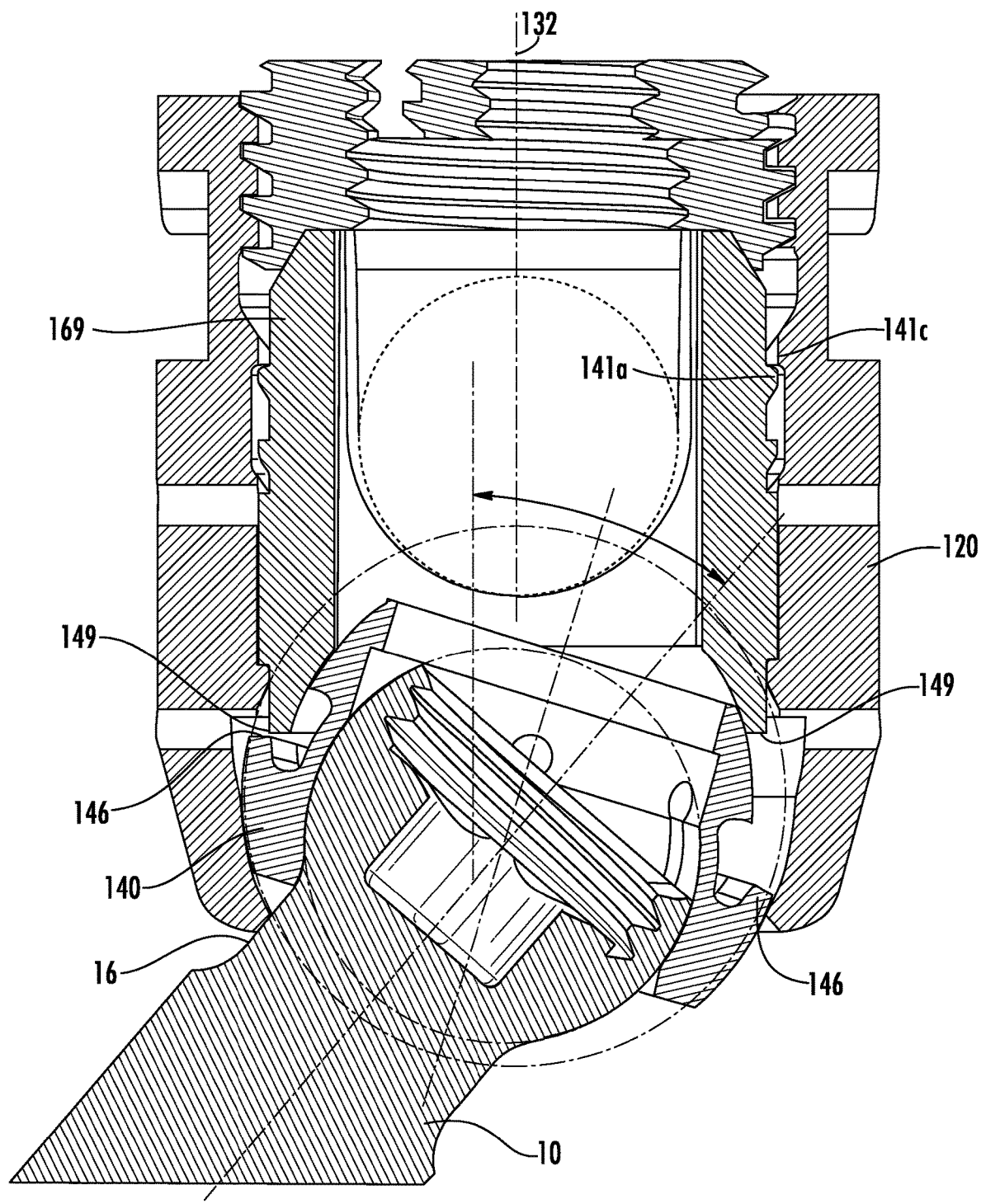

The bushing 140 may thus move within a portion of the axial bore 122 formed in the body 120 between a first (loading/unlocked) position (FIGS. 2A and 2D) and a second (loaded/locked) position (FIGS. 2E-2F). That is, the bushing 140 is moveable within the body 120 between a first position where the bone anchor 10 can be connected to or unconnected from the bushing 140, and the second position where the bushing 140 is locked with respect to the bone anchor 10. The lower end portion 136 of the bushing 140 preferably includes an interior cavity 151 that has a predetermined size to receive and secure the head 14 of the bone anchor 10 so that the bone anchor 10 can rotate polyaxially through a range of angles with respect to the bushing 140 and hence with respect to the body 120 when in an unlocked or loading/unloading position, as shown in FIG. 2F.

As will be described below with reference to FIGS. 4A-4D, the interior cavity 151 formed in the bushing 140 may have a curvate or semi-spherical shape for receiving the curvate or semi-spherical head 14 of the bone anchor 10. The interior cavity 151 formed in the bushing 140 may be constructed so that the bone anchor 10 can polyaxially rotate with respect to the bushing 140, when the bushing is in an unlocked position, and hence, with respect to the body 20. The bushing 140 preferably also includes one or more slots 144 extending from the lower end portion 146 thereof so that at least a portion of the bushing 140 is radially expandable so that the head 14 of the bone anchor 10 can be inserted through the lower opening 142 in the lower end portion 146 and into the interior cavity 151 of the bushing 140 and/or radially compressible to compress or lock against the head 14 of the bone anchor 10 when radial forces are applied thereto. In an implementation, the slots 144 define a plurality of flexible arms 145. The slots 144 may extend from the lower end 146, the upper end 147 or both ends 146, 147. One slot 142 may extend the length of the bushing 140 creating a compressible spring clip.

To interconnect or attach the bone anchor 10 to the body 120, the body 120 may be provided with the bushing 140 pre-assembled and in the loading position, as shown in FIG. 2A. A lower tooth 141*a* of the saddle 169 engages a tooth 41*c* of the body in the locking mechanism 138. The lower surface 173 of the saddle 169 contacts the upper surface 172 of the bushing 140. The head 14 of the bone anchor 10 is inserted into the lower opening 24 of the body 20 and into the interior cavity 51 of the bushing 40. As shown in FIG. 2D, the head 14 is further inserted into the interior cavity 151 of the bushing 140, the head 14 engages the interior surfaces of flexible arms 145. Thus, the head 14 is "snapped-in" to the bushing 140 as the flexible arms 145 frictionally retain the head 14 within the cavity 151.

As shown in FIG. 2E, after the head 14 of the bone anchor 10 is fully inserted into the cavity 151 of the bushing 140, a tool may push down on the saddle 169 to push the bushing 140 further within the lower chamber 136 of the body 120 to prevent the head 14 of the bone anchor 10 from becoming dislodged from bushing 140. The downward movement causes the saddle 169 causes the tooth 141*b* to engage the tooth 141*c* of the body 120. The downward movement also causes the bushing 140 to lock the head 14 of the bone anchor 10 within the cavity 151. As the bushing 140 moves downward by force of the saddle 169, the arms 145 of the bushing 140 come into contact with the one or more lower chamber surfaces 137 in the lower chamber 136 of the body 120, which exert a force against the arms 145 of the bushing 140, causing the arms 145 to be urged around the head 14 of the bone anchor 10 into a locking position, thereby locking the position of the bone anchor 10 relative to the body 120.

Referring to FIG. 2F, when the bone anchor 10 is in the locked position the head 14 is rotatable within the cavity 151. As illustrated, the bushing 140 of the second implementation, provides for approximately 41° of angulation in each direction with respect to the longitudinal axis 32, as both the head 14 and the bushing 140 are rotatable within the lower chamber 136 of the body 120. As illustrated, the neck portion 16 acts as a stop as it contacts the lower end 134 of the bushing 140. Alternatively, the bushing 140 further includes wings 146 that contact ledges 149 of the saddle 169 that may act as a stop to limit the rotational movement of the bushing 140 within the interior cavity 151.

Referring to FIG. 2F, the locking cap 92 is movable from an unlocked to a locked position to lock the bone anchor 10 and the rod (not shown) in place within the body 20. The locking cap of FIG. 2F operates in substantially the same manner as the locking cap described with reference to FIG. 1C.

Thus, the above provides for implementations of a bone fixation assembly that provide for easy securing of the bone anchor within the assembly and for polyaxial rotation of the bone anchor within the bone fixation assembly. In the first and second embodiments, the interaction of the bone anchor, bushing and body have specifically designed sections thereof that come into contact to secure the bone anchor within the bushing. These interactions are further detailed with reference to FIGS. 3-16.

With reference to FIGS. 3A-3E, various configurations of the body 20/120 will now be described. As illustrated, the body may be have the lower end formed as having one of several shapes that may interact with the bushing 40/140. Various configurations of the bushing 40/140 will be introduced in FIGS. 4A-4D. The cooperative engagement of the several configurations of the body 20/120 and the bushing 40/140 are illustrated in FIGS. 5-16.

Figure 3A:
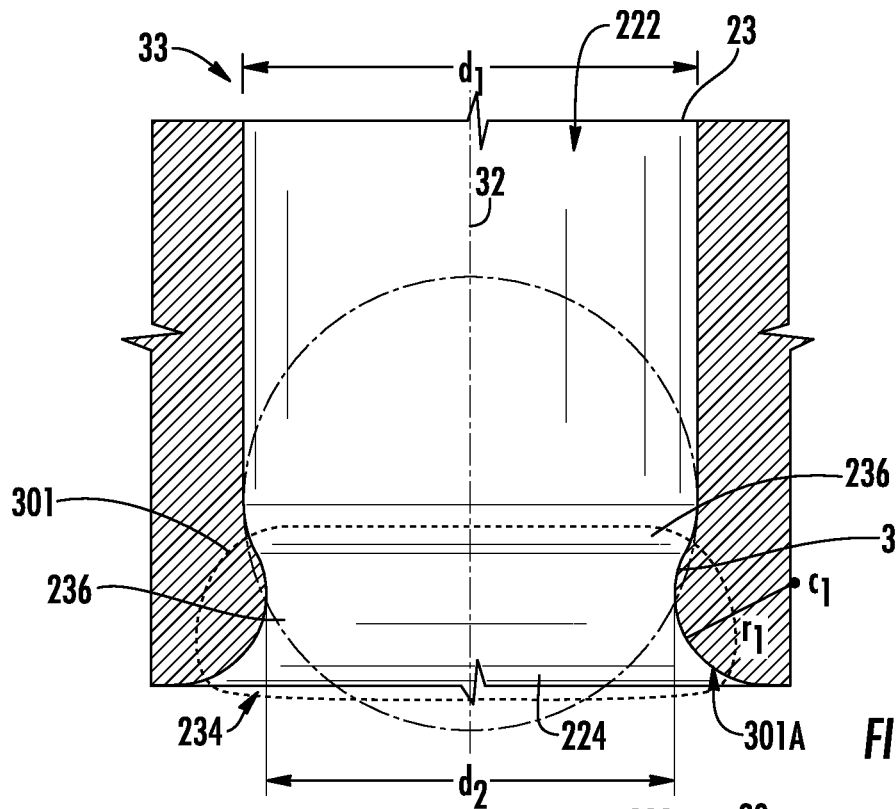

FIG. 3A illustrates a first embodiment of the body 20/120 having a convex lower end 234. In particular, the chamber 236 may be formed as a convex region proximate to the lower opening 224 where the convex region 301 may have a radius of curvature r1 from a center point c1. Thus, a surface 301A of the circle defined by the radius of curvature r1 defines the lower opening 224 as having the diameter d2. The center point c1 may be selected such that the lower opening 224 may taper inwardly along the surface 301A of the circumference, where the taper is toward the longitudinal axis 232.

Figure 3B:
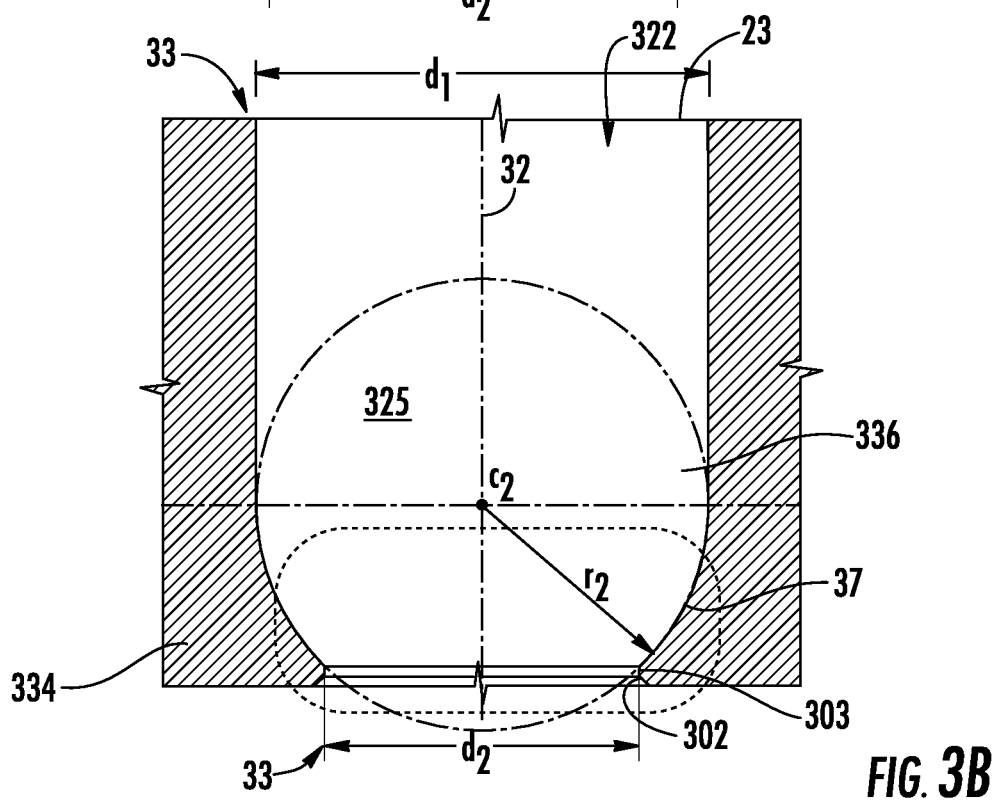

FIG. 3B illustrates a second embodiment of the body 20/120 having a spherical lower end 334. As shown in FIG. 3B, the spherical lower end 334 is formed having a radius r2, as measured from a center point c2 at the longitudinal axis 232. Thus, a spherical region 325 is created within the chamber 336 of the body 20/120 that has a center c2. The lower end 334 may include a tapered region 302 that tapers inwardly to a flat surface 303 that defines the diameter d2 of the lower end 334.

As shown in FIG. 3C, a third embodiment of the body 20/120 having a spherical lower end 334. As shown in FIG. 3C, the spherical lower end 334 is formed having the radius r2, as measured from a center point c2 at the longitudinal axis 232. However, the center point c2 is at location that is shifted upwardly within the chamber 336 of the body 20/120 as compared with the center point c2 in the body 320 of FIG. 3B. Thus, the tapered region 302 that tapers inwardly to the flat surface 303 may be larger than that of FIG. 3B. In accordance with FIG. 3C, the center point c2 may be shifted longitudinally anywhere along the longitudinal axis 232 within the body 20/120.

Alternatively or additionally, as shown in FIGS. 3D and 3E, a non-spherical region 425 within a chamber 446 and having a center c2. The region 425 may be shifted laterally within the body 20/120 such that is at a point along a line that is perpendicular to the longitudinal axis 232. For example, in FIG. 3D the center c2 is shifted to the left of the longitudinal axis 232 (negative), whereas in FIG. 3E, the center c2 is shifted to the right of the longitudinal axis 232 (positive).

Although the body has been explained as having a spherical or non-spherical shape, other shapes may be provided, such as, but not limited to, a conical shape, a torus-like shape, a concave shape or a convex shape.

Figure 4D:
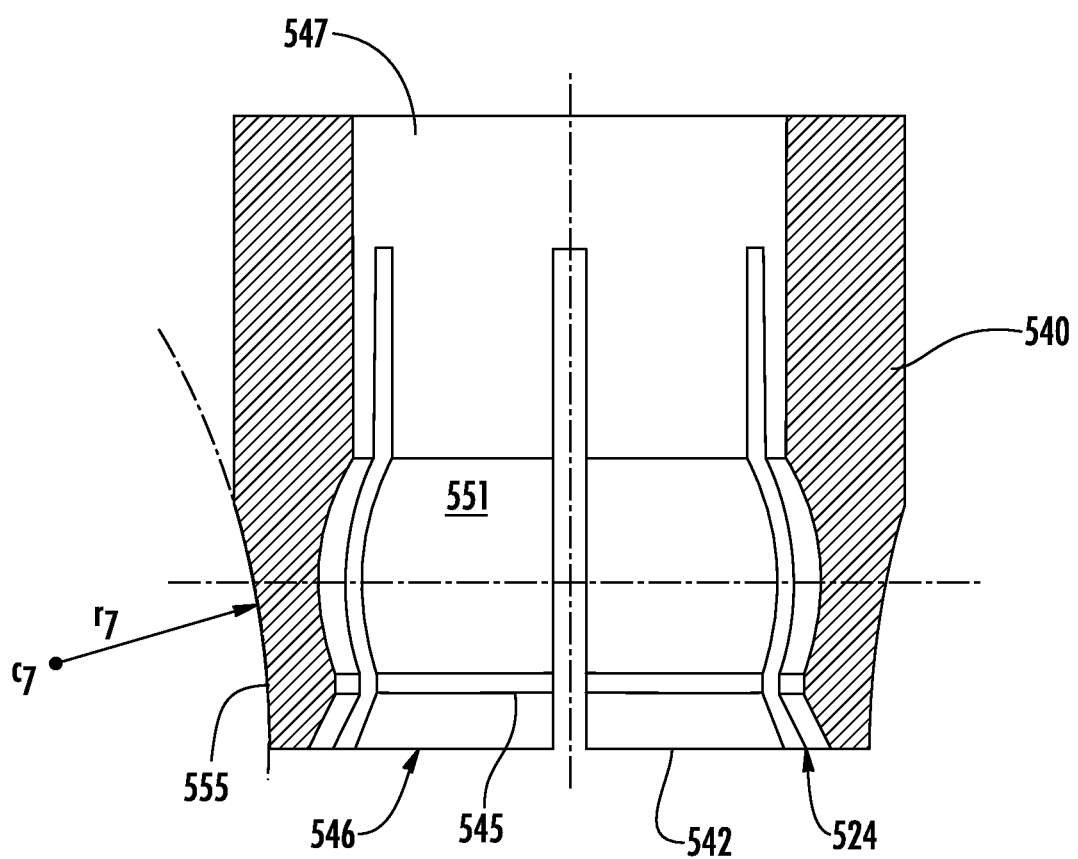

With reference to FIGS. 4A-4D, there is illustrated various configurations of the bushing 40/140. FIG. 4A illustrates a first embodiment of the bushing 240. In the first embodiment, the bushing 240 is provided having a spherical exterior surface 255, which may be sized and configured to contact the lower chamber surfaces of the body. As shown in FIG. 4A, the spherical exterior surface 255 may be defined as portion of a sphere 401 having a radius r4 extending from a center point c4 of a lower end portion 246. The lower end portion 246 includes a lower opening 242 and defines an interior cavity 251 for receiving and securing the head of the bone anchor so that the bone anchor can rotate polyaxially through a range of angles with respect to bushing 240.

FIG. 4B illustrates a second embodiment of the bushing 340 that includes a non-spherical exterior surface 355, which may be sized and configured to contact the lower chamber surfaces of the body. In the embodiment of FIG. 4B, the non-spherical surface 355 is defined by a non-spherical shape 402 having a center c5 that may be shifted to the left of the longitudinal axis 32 (negative). A lower end portion 346 of the bushing 340 includes an interior cavity 351 for receiving and securing the head of the bone anchor through a lower opening 342 so that the bone anchor can rotate polyaxially through a range of angles with respect to the bushing 340.

FIG. 4C illustrates a third embodiment of the bushing 440 that includes a non-spherical exterior surface 455, which may be sized and configured to contact the lower chamber surfaces of the body. In the embodiment of FIG. 4C, the center c6 of the non-spherical exterior 455 is shifted to the right of the longitudinal axis 32 (positive). A lower end portion 446 of the bushing 440 includes an interior cavity 451 for receiving and securing the head of the bone anchor through a lower opening 442 so that the bone anchor can rotate polyaxially through a range of angles with respect to the bushing 440.

FIG. 4D illustrates a fourth embodiment of the bushing 540 that includes a concave exterior surface 555, which may be sized and configured to contact the lower chamber surfaces of the body. The concave exterior surface 555 may be formed having a radius of curvature r7 as measured from a point c7 outside the bushing 540. A lower end portion 546 of the bushing 540 includes an interior cavity 551 for receiving and securing the head of the bone anchor through a lower opening 542 so that the bone anchor can rotate polyaxially through a range of angles with respect to the bushing 540.

For each of the embodiments of the body 20/120 and bushing 40/140 above, the interactions of the exterior surface of the bushing 40/140 and the lower chamber surfaces 37 of the body 20/120 is described below in greater detail. In particular, In accordance with the geometries disclosed in FIGS. 3A-3E and 4A-4D, the various bushings and bodies may be assembled, as shown in FIGS. 1 and 2 to provide interface geometries between the bushing lower exterior surface portions 255, 355, 455 and 555 and the lower chamber surfaces 37 that assume a partially spherical-to-partially spherical interface as well as a linear taper-to-linear taper interface in order to allow the compression of the bushing interior cavity 51 to thereby lock the position and angulation of the bone anchor is locked with respect to the body 20/120 and polyaxial bone fixation assembly 100 as a locking cap is advanced downward through the body 20/120, urging the spinal rod and the bushing disposed therein downward through the body 120 as well. Table 1, below, sets for the example configurations of the body 20/120 and bushing 40/140.

TABLE 1

Figure 5A:
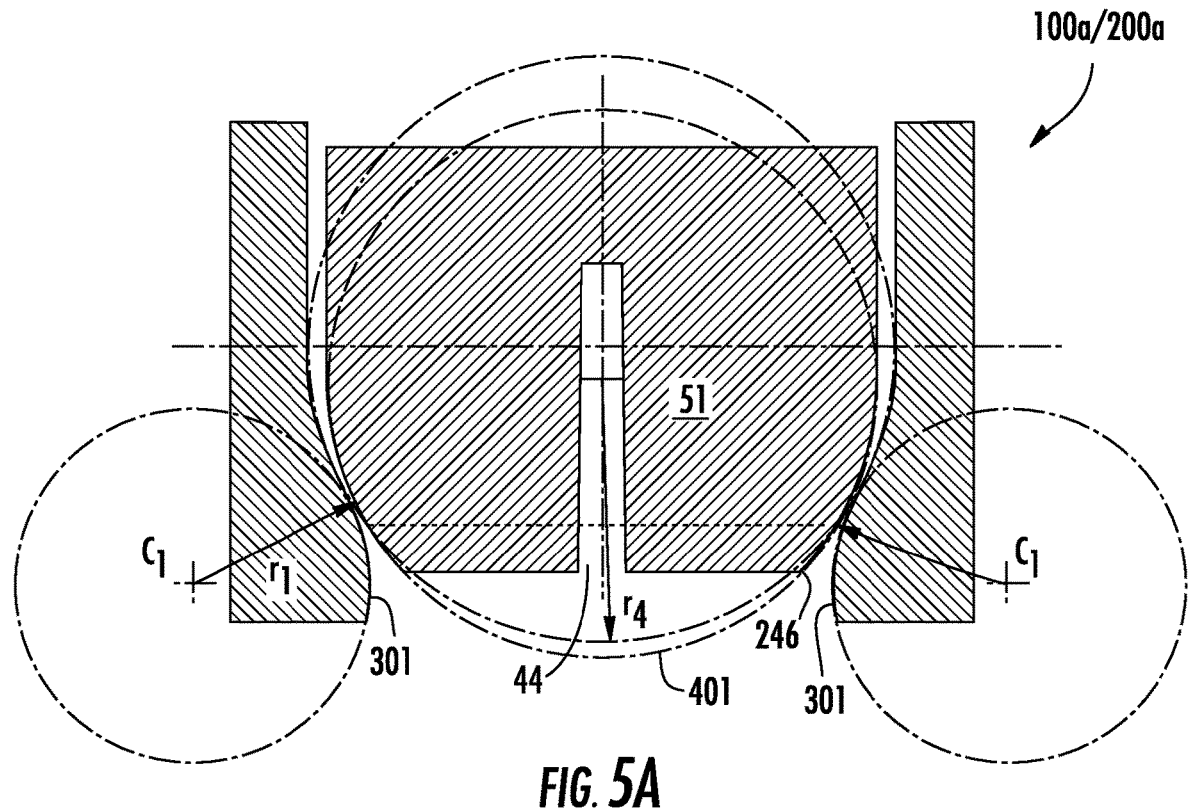
FIGS. 5A-5B illustrate a front sectional view of a first embodiment of a polyaxial pedicle screw assembly of the present disclosure.
Figure 5B:
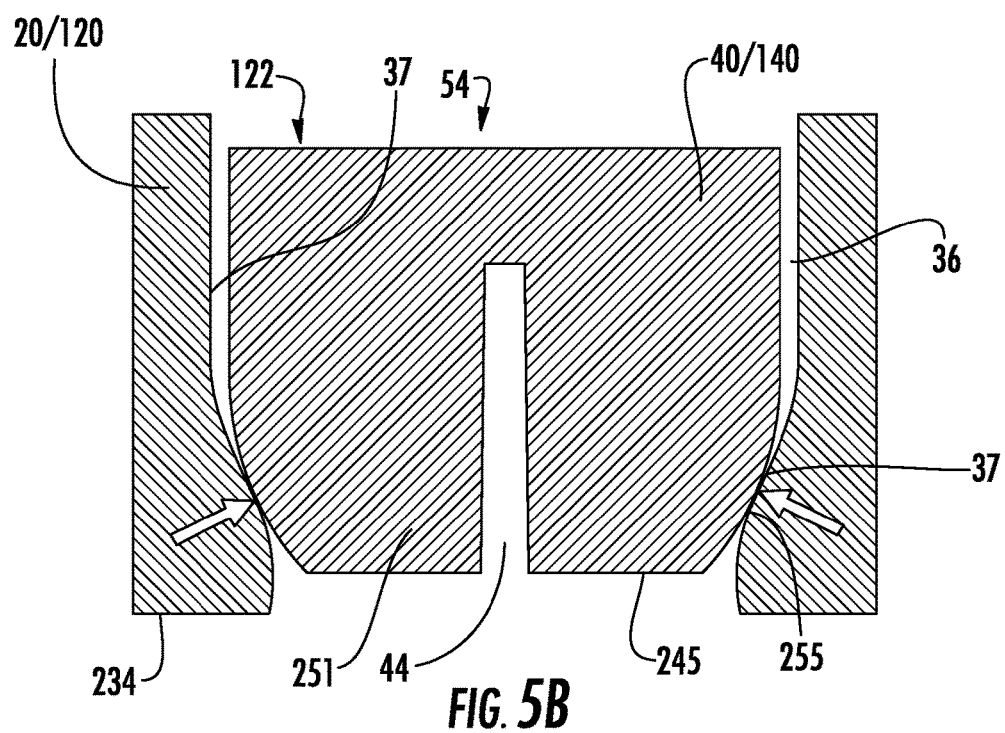
Figure 6A:
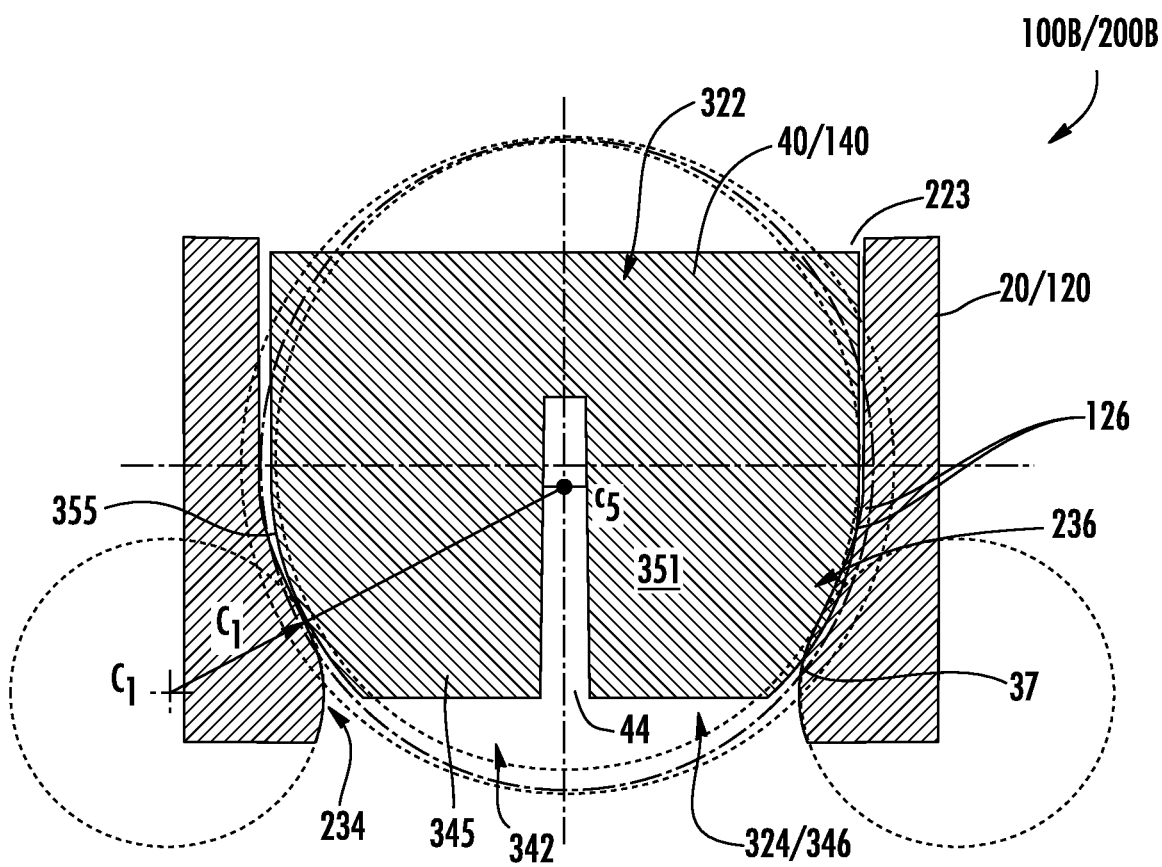
FIGS. 6A-6B illustrate a front sectional view of a second embodiment of a polyaxial pedicle screw assembly of the present disclosure.
Figure 6B:
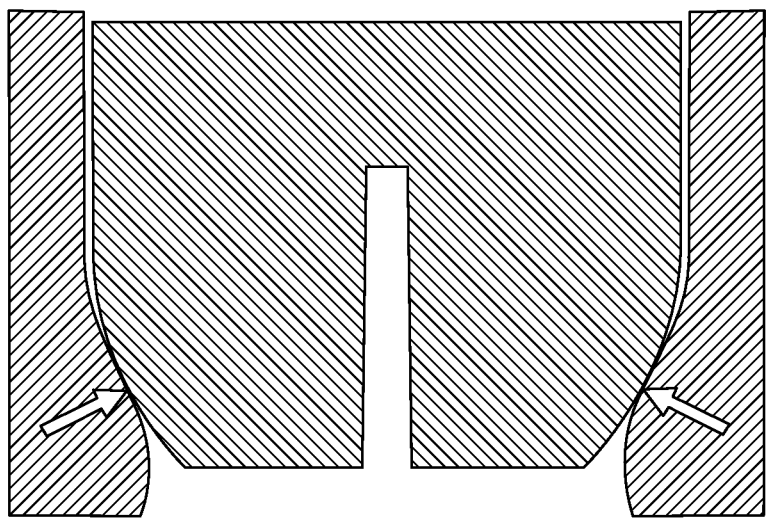
Figure 9A:
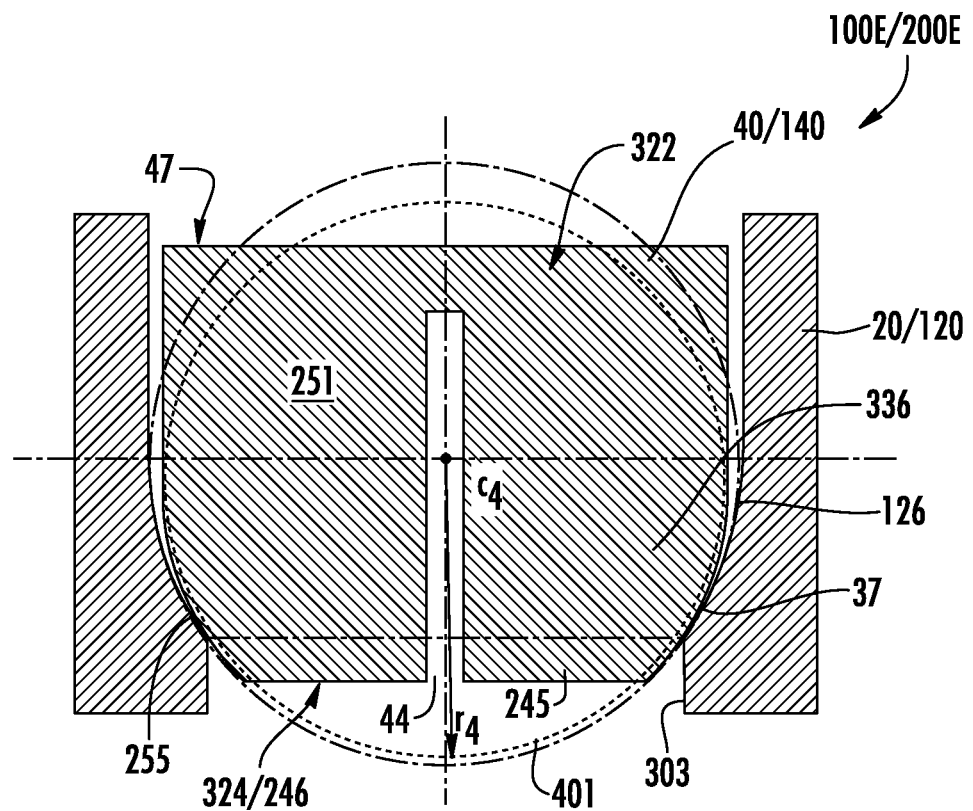
FIGS. 9A-9B illustrate a front sectional view of a fifth embodiment of a polyaxial pedicle screw assembly of the present disclosure.
Figure 9B:
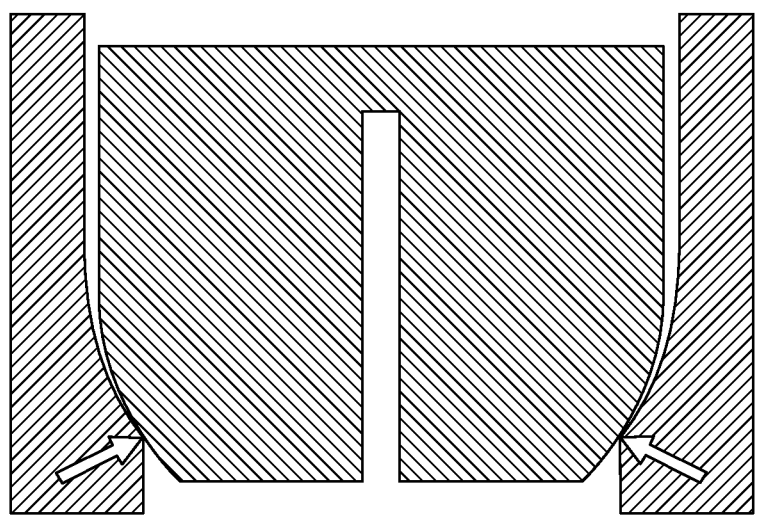
Figure 11A:
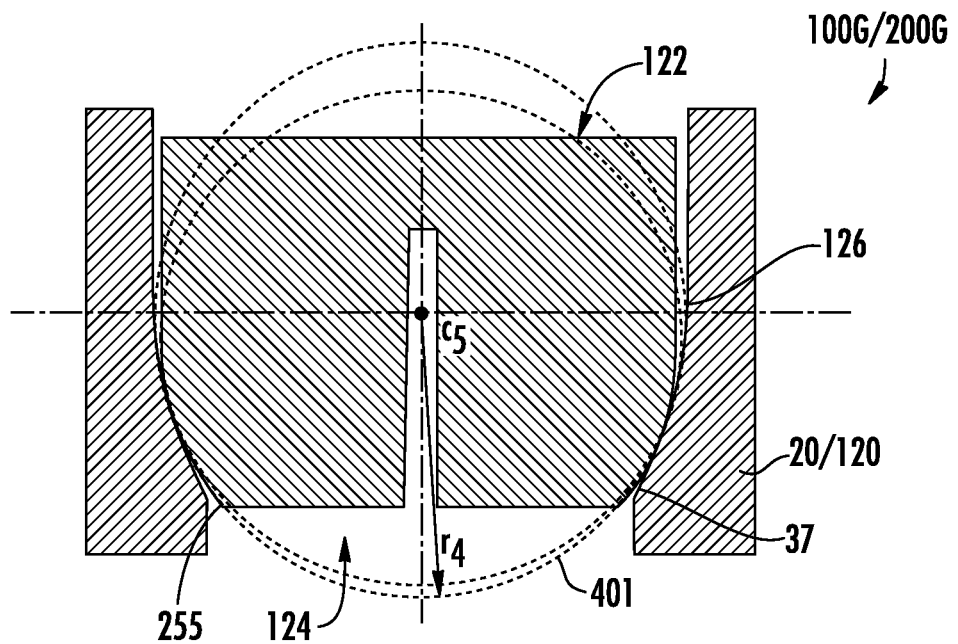
FIGS. 11A-11B illustrate a front sectional view of a seventh embodiment of a polyaxial pedicle screw assembly of the present disclosure.
Figure 11B:
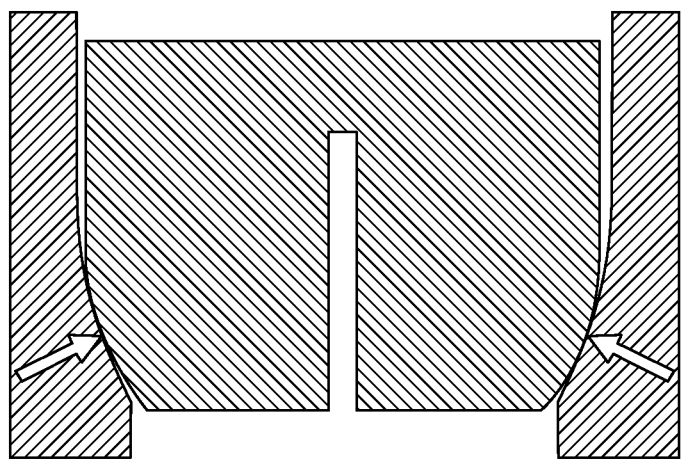
Figure 12A:
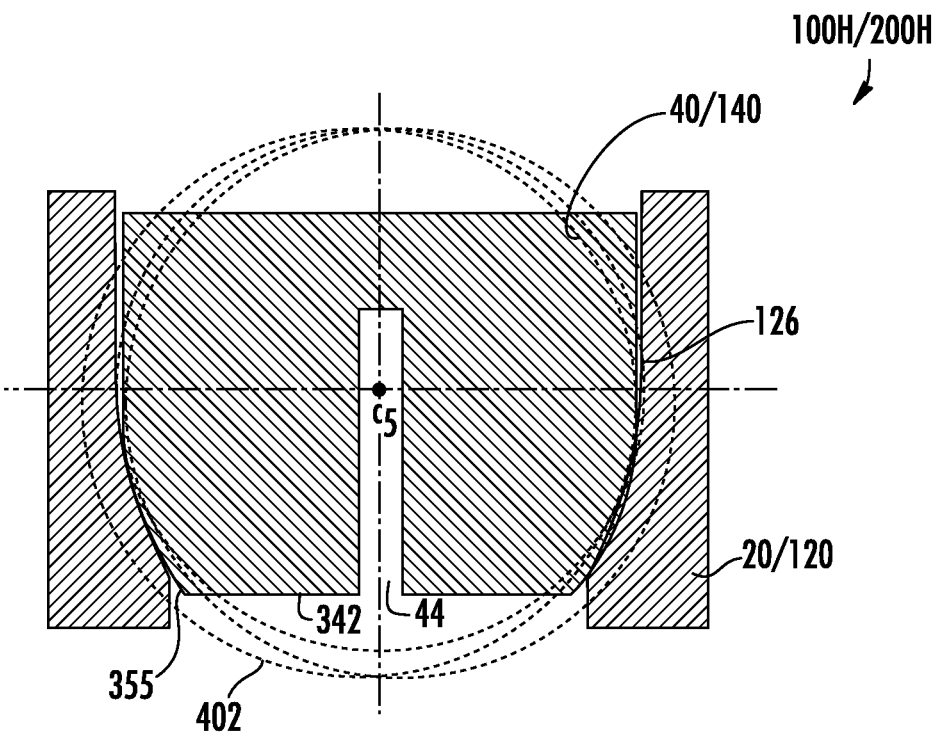
FIGS. 12A-12B illustrate a front sectional view of an eighth embodiment of a polyaxial pedicle screw assembly of the present disclosure.
Figure 12B:
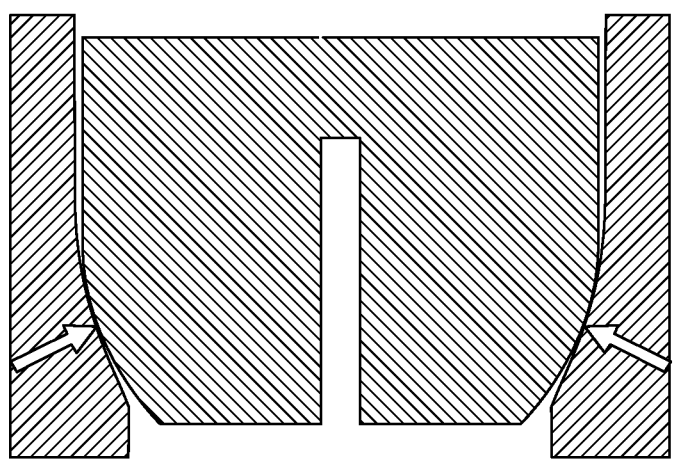
Figure 14:
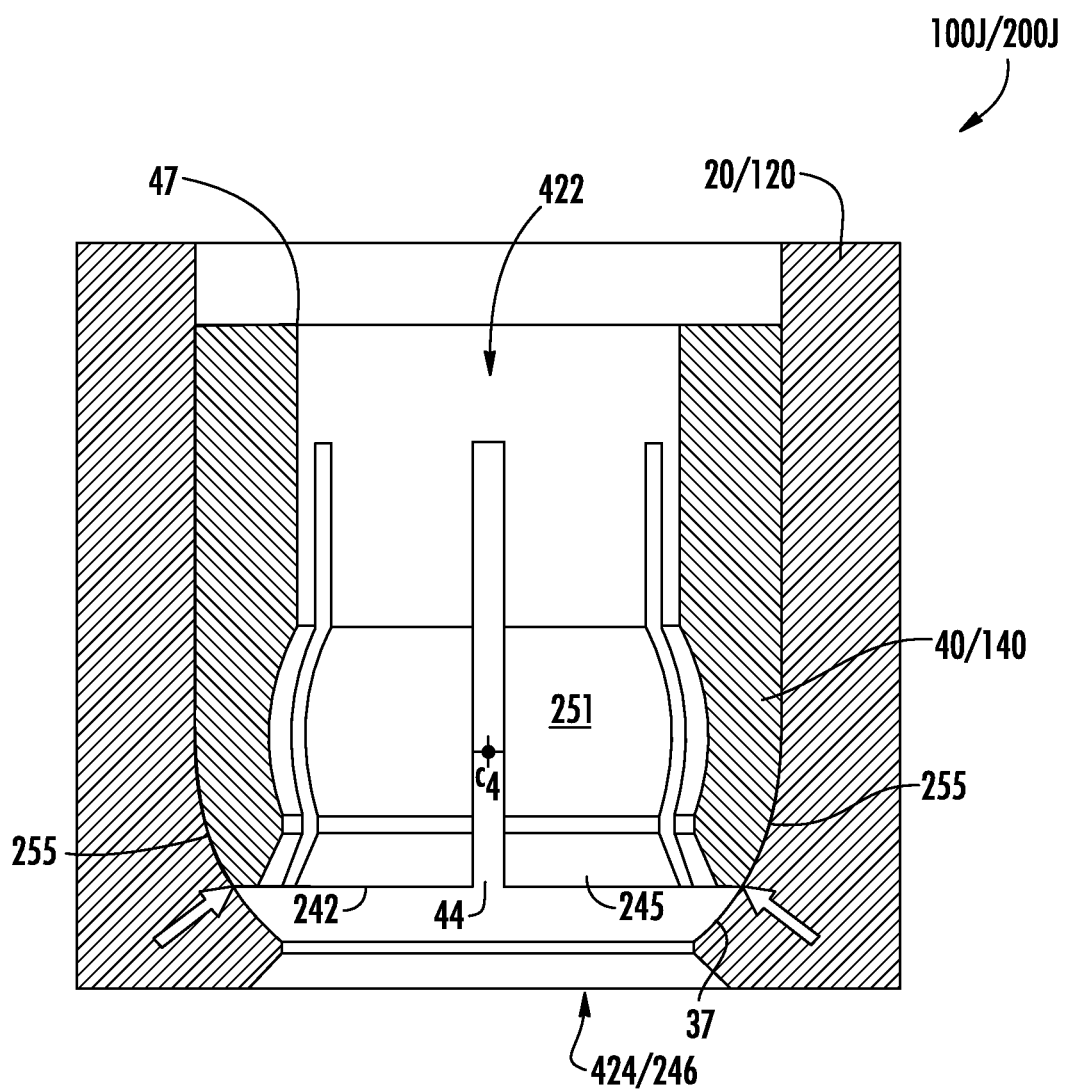
FIG. 14 illustrates a front sectional view of an ninth embodiment of a polyaxial pedicle screw assembly of the present disclosure.
Figure 15A:
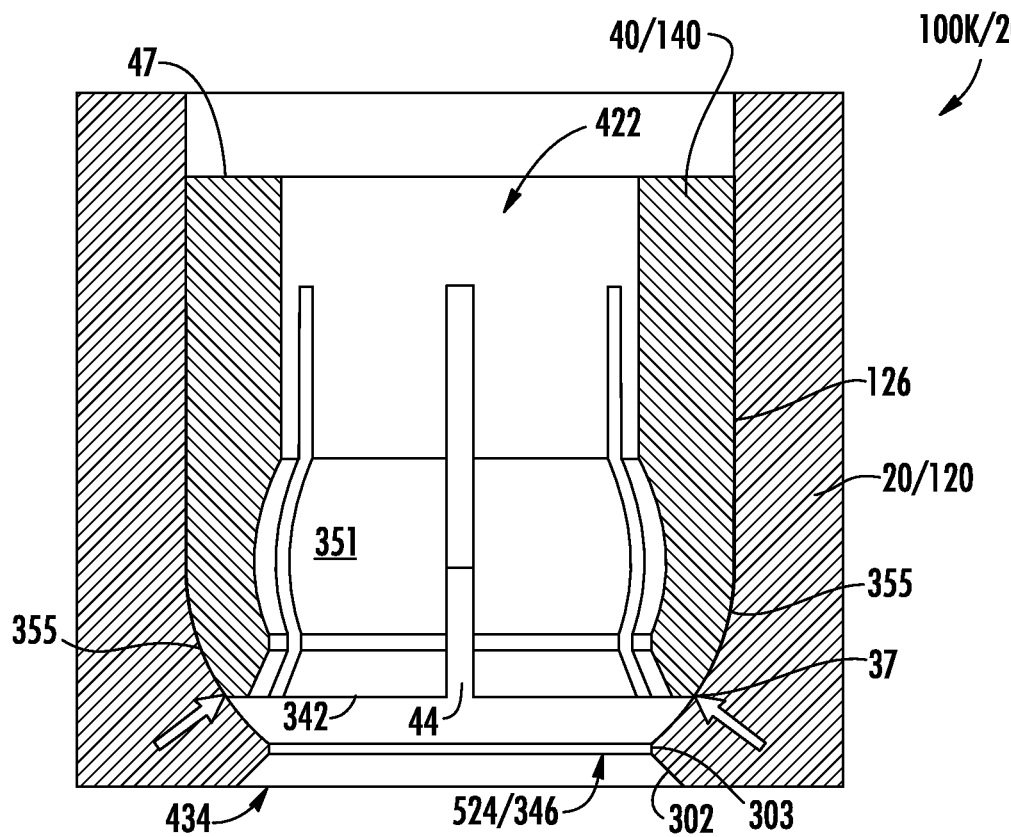
FIGS. 15A-15B illustrate a front sectional view of an tenth embodiment of a polyaxial pedicle screw assembly of the present disclosure.
Figure 15B:
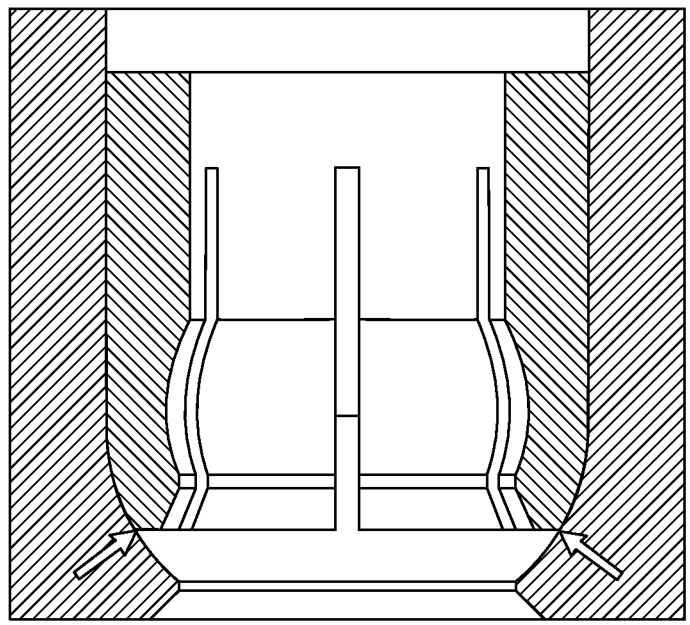

| | | Body 20/120 | | | |
|---|---|---|---|---|---|
| | | Convex | Concave | | |
| Polyaxial Pedical Screw Interface Body/Bushing Matrix | | torus-like (FIG. 3A) | spherical (FIGS. 3B-3C) | torus-like (FIGS. 3D-3E) | Conical |
| Bushing convex 40/140 | spherical (FIG. 4A) | FIGS. 5A-5B | FIGS. 9A-9B | FIG. 14 | FIGS. 11A-11B |
| | torus-like | FIGS. 6A-6B | FIGS. 10A-10B | FIGS. 15A-15B | FIGS. 12A-12B |

TABLE 1-continued

Figure 7A:
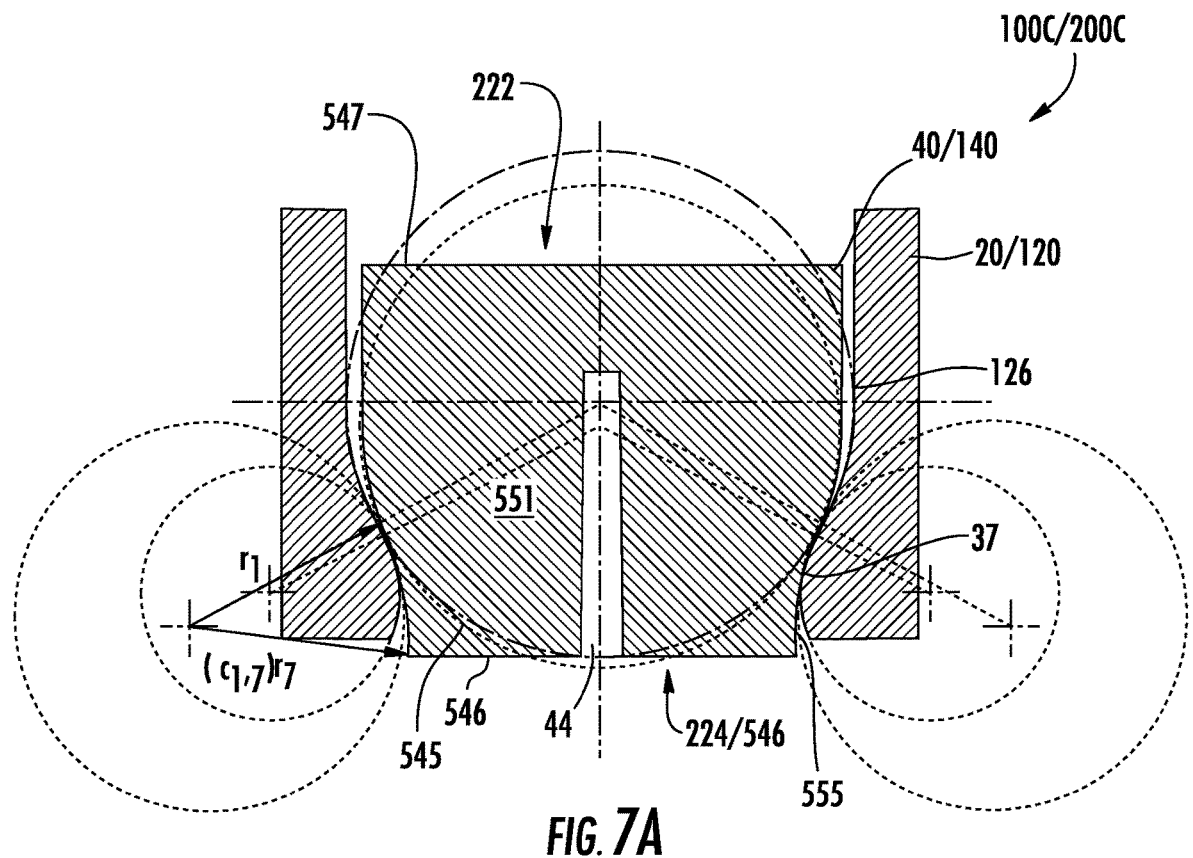
FIGS. 7A-7B illustrate a front sectional view of a third embodiment of a polyaxial pedicle screw assembly of the present disclosure.
Figure 7B:
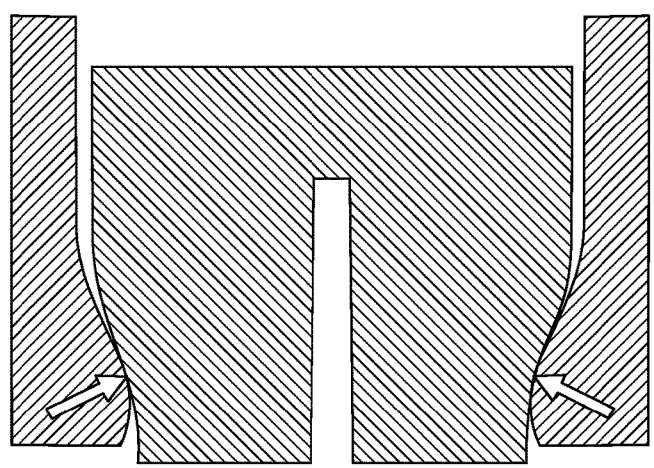
Figure 8A:
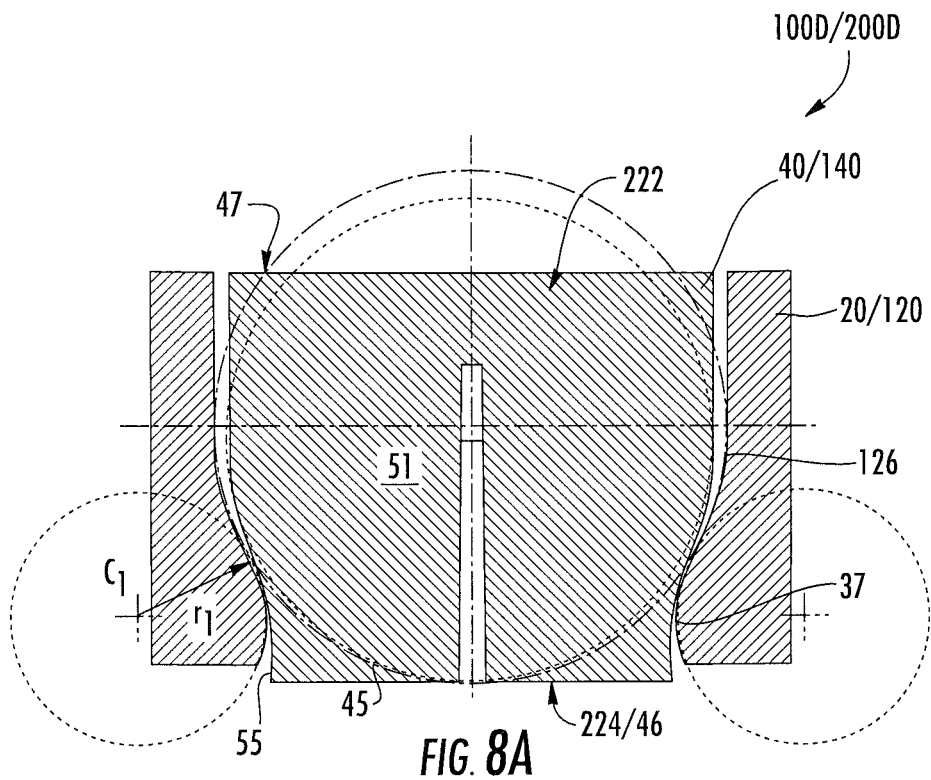
FIGS. 8A-8B illustrate a front sectional view of a fourth embodiment of a polyaxial pedicle screw assembly of the present disclosure.
Figure 8B:
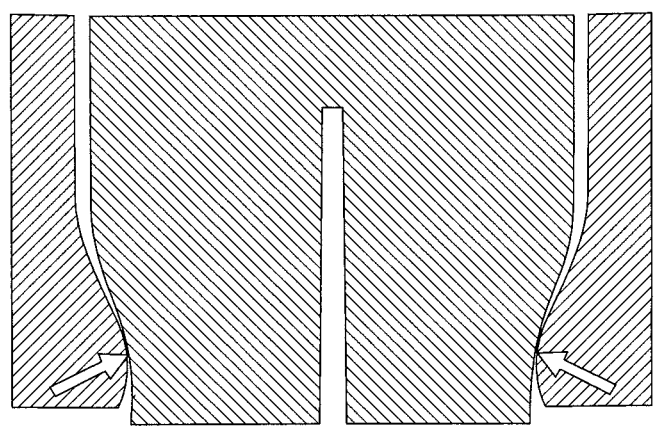
Figure 13:
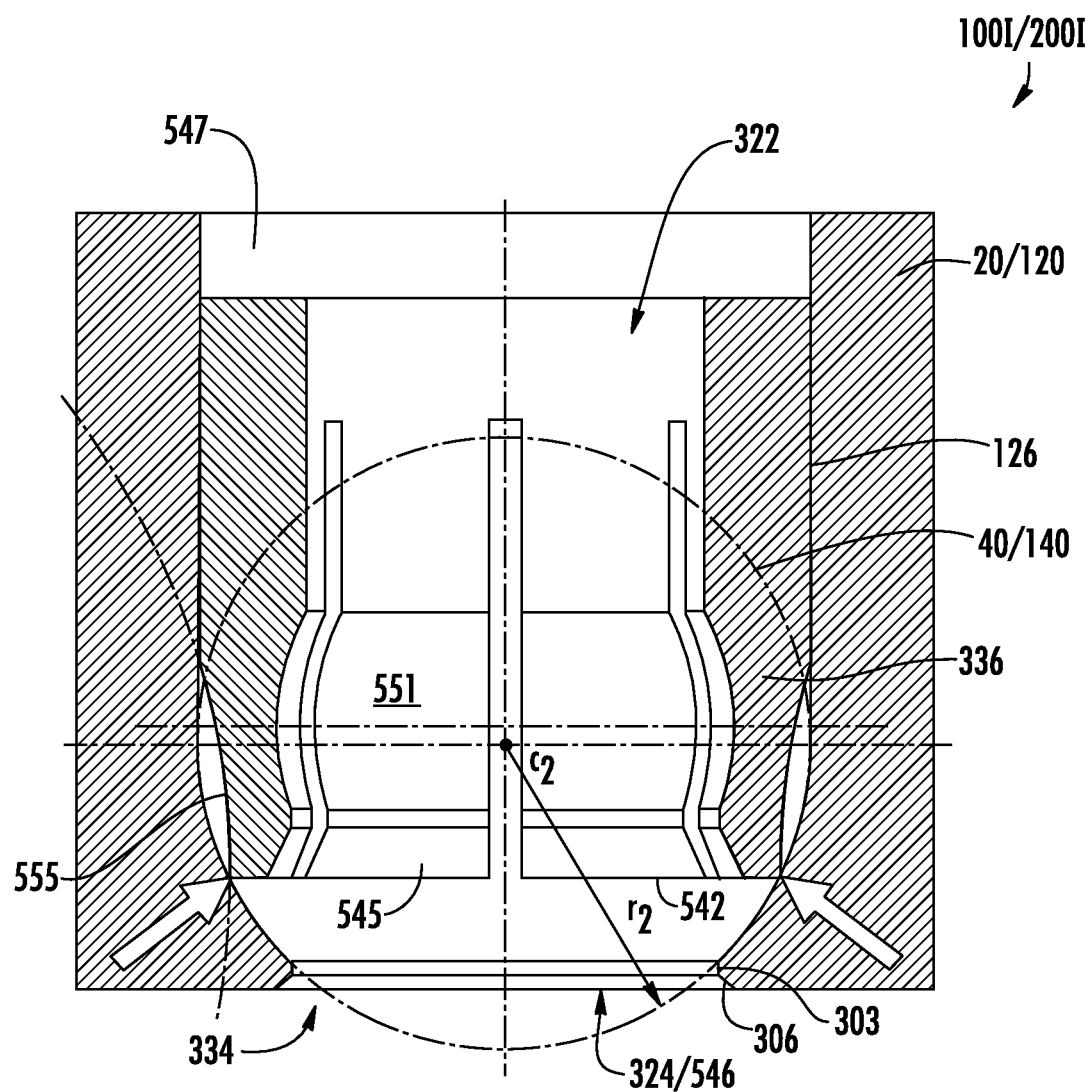
FIG. 13 illustrates a front sectional view of an eighth embodiment of a polyaxial pedicle screw assembly of the present disclosure.

| Polyaxial Pedical Screw Interface Body/Bushing Matrix | Body 20/120 | | | |
|---|---|---|---|---|
| | Convex | Concave | | |
| | torus-like (FIG. 3A) | spherical (FIGS. 3B-3C) | torus-like (FIGS. 3D-3E) | Conical |
| concave torus-like (FIGS. 4B-4C) (FIG. 4D) | FIGS. 7A-7B | FIG. 13 | FIGS. 16A-16B | |
| conical | FIGS 8A-8B | | | |

FIGS. 5A-5B illustrate a front sectional view of a first embodiment of a polyaxial pedicle screw assembly of the present disclosure in which a torus-like convex body lower interior surface portion and a spherical-convex bushing lower exterior surface portion form the bearing surfaces that allow the assembly to be locked FIGS. 5A-5B illustrate a polyaxial bone fixation assembly 100A/200A that includes a body 20/120 having an axial bore characterized by a generally cylindrical interior geometry adjacent the axial bore 122 and characterized by a torus-like convex interior geometry along the lower chamber surfaces 37 adjacent the lower opening 124. More specifically, as can best be seen taking into account the dotted circles of FIG. 5A, the lower chamber surfaces 37 progresses from an essentially cylindrical surface adjacent the body axial bore 122 and transitions through a hemi-concave surface tracing out approximately 45 degrees and smoothly inflects to a hemi-convex surface tracing out approximately 45 degrees adjacent the body lower opening 124.

The bushing 40/140 is characterized by an exterior surface 55 that assumes a generally cylindrical geometry adjacent the upper end 47 and smoothly transitions to a spherical convex geometry or hemi-convex surface along the lower exterior surface portion 255 and adjacent to the lower end 241. As the bushing 40/140 is urged downward through the polyaxial bone fixation assembly 100 and the lower exterior surface portion 255 bears against the lower chamber surfaces 37 of the body 120, the interior cavity 51 is locked around the head of the bone anchor as the flexible arms 45 are drawn together and the position and angulation of the bone anchor is locked with respect to the body 120 and polyaxial bone fixation assembly 100. The dark arrows show in FIG. 5B illustrate a point of contact between the body 20/120 and the bushing 40/140 when in the locked state.

FIGS. 6A-6B illustrate a front sectional view of a second embodiment of a polyaxial pedicle screw assembly of the present disclosure in which a torus-like convex body lower interior surface portion and a torus-convex bushing lower exterior surface portion form the bearing surfaces that allow the assembly to be locked. FIGS. 6A-6B illustrate a polyaxial bone fixation assembly 100B/200B that includes a body 20/120 having an axial bore characterized by a generally cylindrical interior geometry adjacent the axial bore 322 and characterized by a torus-like convex interior geometry at the lower chamber surfaces 37 adjacent the lower end 324. More specifically, as can best be seen taking into account the dotted circles of FIG. 6A, the body interior surface 126 progresses from an essentially cylindrical surface adjacent the body axial bore 222 and transitions through a hemi-concave surface tracing out approximately 45 degrees and smoothly inflects to a hemi-convex surface tracing out approximately 45 degrees adjacent the body lower opening 224.

The bushing 40/140 is characterized by an exterior surface 355 that assumes a generally cylindrical geometry adjacent the upper end 47 and smoothly transitions to a torus-like convex geometry or hemi-convex surface along the lower exterior surface portion 355 and adjacent to the lower end portion 346. As the bushing is urged downward through the polyaxial bone fixation assembly 100B/200B and the lower exterior surface portion 355 bears against the lower chamber surfaces 37 of the body 20/120, the interior cavity 351 is crush locked around the head of the bone anchor as the flexible arms 345 are drawn together and the position and angulation of the bone anchor is locked with respect to the body 20/120 and polyaxial bone fixation assembly 100B/200B. The dark arrows show in FIG. 6B illustrate a point of contact between the body 20/120 and the bushing 40/140 when in the locked state.

FIGS. 7A-7B illustrate a front sectional view of a third embodiment of a polyaxial pedicle screw assembly of the present disclosure in which a torus-like convex body lower interior surface portion and a torus-like concave bushing lower exterior surface portion form the bearing surfaces that allow the assembly to be locked, FIGS. 7A-7B illustrate a polyaxial bone fixation assembly 100C/200C that includes a body 20/120 having an axial bore characterized by a generally cylindrical interior geometry adjacent the axial bore 222 and characterized by a torus-like convex interior geometry at the lower chamber surfaces 37 adjacent the lower opening 224. More specifically, as can best be seen taking into account the dotted circles of FIG. 7A, the body interior surface 126 progresses from an essentially cylindrical surface adjacent the body axial bore 222 and transitions through a hemi-concave surface tracing out approximately 45 degrees and smoothly inflects to a partially-convex surface tracing out approximately 45 degrees adjacent the body lower opening 224.

The bushing 40 is characterized by an exterior surface 555 that assumes a generally cylindrical geometry adjacent the upper end 547 and smoothly transitions to a torus-like concave geometry along the lower exterior surface portion 555 and adjacent the lower end portion 546. As the bushing 40/140 is urged downward through the polyaxial bone fixation assembly 100 and the lower exterior surface portion 555 bears against the lower chamber surfaces 37 of the body 20/120, the interior cavity 551 is crush locked around the head of the bone anchor as the flexible arms 545 are drawn together and the position and angulation of the bone anchor is locked with respect to the body 20/120 and the polyaxial bone fixation assembly 100C/200C. The dark arrows show in FIG. 7B illustrate a point of contact between the body 20/120 and the bushing 40/140 when in the locked state.

FIGS. 8A-8B illustrate a front sectional view of a fourth embodiment of a polyaxial pedicle screw assembly of the present disclosure in which a torus-like convex body lower interior surface portion and a conical bushing lower exterior surface portion form the bearing surfaces that allow the assembly to be locked. FIGS. 8A-8B illustrate a polyaxial bone fixation assembly 100D/200D that includes a body 20/120 having an axial bore characterized by a generally cylindrical interior geometry adjacent the axial bore 222 and characterized by a torus-like convex interior geometry at the lower chamber surfaces 37 adjacent the lower opening 224. More specifically, as can best be seen taking into account the dotted circles of FIG. 8A, the body interior surface 126 progresses from an essentially cylindrical surface adjacent the body axial bore 222 and transitions through a hemi-concave surface tracing out approximately 45 degrees and smoothly inflects to a partially-convex surface tracing out approximately 45 degrees adjacent the body lower opening 224.

The bushing 40/140 is characterized by an exterior surface 55 that assumes a generally cylindrical geometry adjacent the upper end 47 and smoothly transitions through a conical taper along the bushing lower exterior surface portion 55 prior to terminating in a cylindrical geometry adjacent the bushing lower end portion 46. As the bushing 40/140 is urged downward through the polyaxial bone fixation assembly 100C/200D and the conical taper disposed along the lower exterior surface portion 255, 355, 455 and 555 bears against the lower chamber surfaces 37 of the body 20/120, the interior cavity 51 is crush locked around the head of the bone anchor as the flexible arms 45 are drawn together and the position and angulation of the bone anchor is locked with respect to the body 20/120 and the polyaxial bone fixation assembly 100D/200D. The dark arrows show in FIG. 8B illustrate a point of contact between the body 20/120 and the bushing 40/140 when in the locked state.

FIGS. 9A-9B illustrate a front sectional view of a fifth embodiment of a polyaxial pedicle screw assembly of the present disclosure in which a spherical-concave body lower interior surface portion and a spherical-convex bushing lower exterior surface portion form the bearing surfaces that allow the assembly to be locked. FIGS. 9A-9B illustrate a polyaxial bone fixation assembly 100E/200E that includes a body 20/120 having an axial bore characterized by a generally cylindrical interior geometry adjacent the axial bore 322 and terminating in a generally cylindrical interior geometry adjacent the lower opening 324 having a radius smaller than the radius characterizing the axial bore at the axial bore 322. Prior to terminating in the cylindrical geometry at the lower opening 324, the axial bore is characterized by a spherical concave surface geometry along the lower chamber surfaces 37. More specifically, as can best be seen taking into account the dotted circles in FIG. 9A, the body interior surface 126 progresses from an essentially cylindrical surface adjacent the body axial bore 322 and smoothly transitions through a hemi-concave surface along the body lower chamber surfaces 37 tracing out approximately 45 degrees and transitions to an essentially cylindrical surface adjacent the body lower opening 324, the radius of the cylindrical surface adjacent the body lower opening 324 being smaller than the radius of the cylindrical surface adjacent the body axial bore 322.

The bushing 40/140 is characterized by an exterior surface 255 that assumes a generally cylindrical geometry adjacent the upper end 47 and smoothly transitions to a spherical-convex, or hemi-convex, surface along the bushing lower exterior surface portion 255 tracing out an angle of approximately 45 degrees that terminates at the bushing lower end portion 246. As the bushing 40/140 is urged downward through the polyaxial bone fixation assembly 100 and the lower exterior surface portion 255 bears against the lower chamber surfaces 37 of the body 20/120, the interior cavity 251 is crush locked around the head of the bone anchor as the flexible arms 245 are drawn together and the position and angulation of the bone anchor is locked with respect to the body 20/120 and the polyaxial bone fixation assembly 100E/200E. The dark arrows show in FIG. 9B illustrate a point of contact between the body 20/120 and the bushing 40/140 when in the locked state.

FIGS. 10A-10B illustrate a front sectional view of a sixth embodiment of a polyaxial pedicle screw assembly of the present disclosure in which a spherical-concave body lower interior surface portion and a torus-like convex bushing lower exterior surface portion form the bearing surfaces that allow the assembly to be locked. FIGS. 10A-10B illustrate a polyaxial bone fixation assembly 100F/200F that includes a body 20/120 having an axial bore characterized by a generally cylindrical interior geometry adjacent the axial bore 322 and terminating in a generally cylindrical interior geometry adjacent the lower opening 324 having a radius smaller than the radius characterizing the axial bore at the axial bore 322. Prior to terminating in the cylindrical geometry at the lower opening 324, the axial bore is characterized by a spherical concave surface geometry along the lower chamber surfaces 37. More specifically, as can best be seen taking into account the dotted circles in FIG. 10A, the body interior surface 126 progresses from an essentially cylindrical surface adjacent the body axial bore 322 and smoothly transitions through a hemi-concave surface along the body lower chamber surfaces 37 tracing out approximately 45 degrees and transitions to an essentially cylindrical surface adjacent the body lower opening 324, the radius of the cylindrical surface adjacent the body lower opening 324 being smaller than the radius of the cylindrical surface adjacent the body axial bore 322.

The bushing 40/140 is characterized by an exterior surface 355 that assumes a generally cylindrical geometry adjacent the bushing upper end 347 and smoothly transitions to a torus-like convex, or hemi-convex, surface along the bushing lower exterior surface portion 355 tracing out an angle of approximately 45 degrees that terminates at the bushing lower end portion 346. As the bushing is urged downward through the polyaxial bone fixation assembly 100F/200F and the lower exterior surface portion 355 bears against the lower chamber surfaces 37 of the body 20/120, the interior cavity 351 is crush locked around the head of the bone anchor as the flexible arms 345 are drawn together and position and angulation of the bone anchor is locked with respect to the body 20/120 and the polyaxial bone fixation assembly 100F/200F. The dark arrows show in FIG. 10B illustrate a point of contact between the body 20/120 and the bushing 40/140 when in the locked state.

FIGS. 11A-11B illustrate a front sectional view of a seventh embodiment of a polyaxial pedicle screw assembly of the present disclosure in which a conical body lower interior surface portion and a spherical-convex bushing lower exterior surface portion form the bearing surfaces that allow the assembly to be locked. FIGS. 11A-11B illustrate a polyaxial bone fixation assembly 100G/200G that includes a body 20/120 having an axial bore characterized by a generally cylindrical interior geometry adjacent the axial bore 122 and terminating in a cylindrical interior geometry adjacent the lower opening 124 having a radius smaller than the radius characterizing the axial bore at the axial bore 122. Prior to terminating in the cylindrical geometry at the lower opening 124, the axial bore is characterized by a conical surface geometry that provides a linear taper along the lower chamber surfaces 37. More specifically, as can best be seen taking into account the dotted circles in FIG. 11A, the body interior surface 126 progresses from an essentially cylindrical surface adjacent the body axial bore 122 and transitions to a conical surface geometry along the body lower chamber surfaces 37 and transitions back to an essentially cylindrical surface adjacent the body lower opening 124, the radius of the cylindrical surface adjacent the body lower opening 124 being smaller than the radius of the cylindrical surface adjacent the body axial bore 122.

The bushing 40/140 is characterized by an exterior surface 255 that assumes a generally cylindrical geometry adjacent the upper end 47 and smoothly transitions to a spherical-convex, or hemi-convex, surface along the bushing lower exterior surface portion 255 tracing out an angle of approximately 45 degrees that terminates at the bushing lower end portion 246. As the bushing 40/140 is urged downward through the polyaxial bone fixation assembly 100G/200G and the bushing lower exterior surface portion 255 bears against the body lower chamber surfaces 37, the interior cavity 251 is crush locked around the head of the bone anchor as the flexible arms 245 are drawn together and the position and angulation of the bone anchor is locked with respect to the body 20/120 and the polyaxial bone fixation assembly 100G/200G. The dark arrows show in FIG. 11B illustrate a point of contact between the body 20/120 and the bushing 40/140 when in the locked state.

FIGS. 12A-12B illustrate a front sectional view of an eighth embodiment of a polyaxial pedicle screw assembly of the present disclosure in which a conical body lower interior surface portion and a torus-like convex bushing lower exterior surface portion form the bearing surfaces that allow the assembly to be locked. FIGS. 12A-12B illustrate a polyaxial bone fixation assembly 100H/200H that includes a body 20/120 having an axial bore characterized by a generally cylindrical interior geometry adjacent the axial bore 122 and terminating in a cylindrical interior geometry adjacent the lower opening 124 having a radius smaller than the radius characterizing the axial bore at the axial bore 122. Prior to terminating in the cylindrical geometry at the lower opening 124, the axial bore is characterized by a conical surface geometry that provides a linear taper along the lower chamber surfaces 37. More specifically, as can best be seen taking into account the dotted circles in FIG. 12A, the body interior surface 126 progresses from an essentially cylindrical surface adjacent the body axial bore 122 and transitions to a conical surface geometry along the body lower chamber surfaces 37 and transitions back to an essentially cylindrical surface adjacent the body lower opening 124, the radius of the cylindrical surface adjacent the body lower opening 124 being smaller than the radius of the cylindrical surface adjacent the body axial bore 122.

The bushing 40/140 is characterized by an exterior surface 355, 455 that assumes a generally cylindrical geometry adjacent the bushing upper end 47 and smoothly transitions to a torus-like convex, or hemi-convex, surface along the lower exterior surface portion 355 tracing out an angle of approximately 45 degrees that terminates at the bushing lower end portion 346, 446. As the bushing 40/140 is urged downward through the polyaxial bone fixation assembly 100H/200H and the bushing lower exterior surface portion 355 bears against the lower chamber surfaces 37, the interior cavity 351, 451 is crush locked around the head of the bone anchor as the flexible arms 345, 445 are drawn together and the position and angulation of the bone anchor is locked with respect to the body 20/120 and the polyaxial bone fixation assembly 100H/200H. The dark arrows show in FIG. 12B illustrate a point of contact between the body 20/120 and the bushing 40/140 when in the locked state.

FIG. 13 illustrates a polyaxial bone fixation assembly 100I/200I that includes a body 20/120 having an axial bore characterized by a generally cylindrical interior geometry adjacent the axial bore 322 and terminating in a generally cylindrical interior geometry adjacent the lower opening 324 having a radius smaller than the radius characterizing the axial bore at the axial bore 322. Prior to terminating in the cylindrical geometry at the lower opening 324, the axial bore is characterized by a spherical concave surface geometry along the lower chamber surfaces 37. The body interior surface 126 progresses from an essentially cylindrical surface adjacent the body axial bore 322 and smoothly transitions through a hemi-concave surface along the body lower chamber surfaces 37 tracing out approximately 45 degrees and transitions to an essentially cylindrical surface adjacent the body lower opening 324, the radius of the cylindrical surface adjacent the body lower opening 324 being smaller than the radius of the cylindrical surface adjacent the body axial bore 322.

The bushing 40/140 is characterized by an exterior surface 555 that assumes a generally cylindrical geometry adjacent the upper end 547 and smoothly transitions to a torus-like concave geometry along the lower exterior surface portion 555 and adjacent the lower end portion 546. As the bushing 40/140 is urged downward through the polyaxial bone fixation assembly 100I/200I and the lower exterior surface portion 555 bears against the lower chamber surfaces 37 of the body 20/120, the interior cavity 551 is crush locked around the head of the bone anchor as the flexible arms 545 are drawn together and the position and angulation of the bone anchor is locked with respect to the body 20/120 and the polyaxial bone fixation assembly 100I/200I. The dark arrows show in FIG. 13 illustrate a point of contact between the body 20/120 and the bushing 40/140 when in the locked state.

FIG. 14 illustrates a polyaxial bone fixation assembly 100J/200J that includes a body 20/120 having an axial bore characterized by a generally cylindrical interior geometry adjacent the axial bore 422 and characterized by a torus-like concave interior geometry along the lower chamber surfaces 37 adjacent the lower opening 424. More specifically, the lower chamber surfaces 37 progresses from an essentially cylindrical surface adjacent the body axial bore 422 and transitions through a hemi-concave surface tracing out approximately 45 degrees and smoothly inflects to a hemi-concave surface tracing out approximately 45 degrees adjacent the body lower opening 424.

The bushing 40/140 is characterized by an exterior surface 255 that assumes a generally cylindrical geometry adjacent the upper end 47 and smoothly transitions to a spherical concave geometry or hemi-concave surface along the lower exterior surface portion 255 and adjacent to the lower end portion 246. As the bushing 40/140 is urged downward through the polyaxial bone fixation assembly 100 and the lower exterior surface portion 255 bears against the lower chamber surfaces 37 of the body 20/120, the interior cavity 251 is crush locked around the head of the bone anchor as the flexible arms 245 are drawn together and the position and angulation of the bone anchor is locked with respect to the body 20/120 and polyaxial bone fixation assembly 100J/200J. The dark arrows show in FIG. 14 illustrate a point of contact between the body 20/120 and the bushing 40/140 when in the locked state.

FIGS. 15A-15B illustrate a polyaxial bone fixation assembly 100K/200K that includes a body 20/120 having an axial bore characterized by a generally cylindrical interior geometry adjacent the axial bore 422 and characterized by a torus-like concave interior geometry at the lower chamber surfaces 37 adjacent the lower end 524. More specifically, the body interior surface 126 progresses from an essentially cylindrical surface adjacent the body axial bore 422 and transitions through a hemi-concave surface tracing out approximately 45 degrees and smoothly inflects to a hemi-concave surface tracing out approximately 45 degrees adjacent the body lower opening 524.

The bushing 40/140 is characterized by an exterior surface 355 that assumes a generally cylindrical geometry adjacent the upper end 47 and smoothly transitions to a torus-like concave geometry or hemi-concave surface along the lower exterior surface portion 355 and adjacent to the lower end portion 346. As the bushing is urged downward through the polyaxial bone fixation assembly 100K/200K and the lower exterior surface portion 355 bears against the lower chamber surfaces 37 of the body 20/120, the interior cavity 351 is crush locked around the head of the bone anchor as the flexible arms 45 are drawn together and the position and angulation of the bone anchor is locked with respect to the body 20/120 and polyaxial bone fixation assembly 100K/200K. The dark arrows show in FIGS. 15A and 15B illustrate a point of contact between the body 20/120 and the bushing 40/140 when in the locked state.

FIGS. 16A-16B illustrate a polyaxial bone fixation assembly 100L/200L that includes a body 20/120 having an axial bore characterized by a generally cylindrical interior geometry adjacent the axial bore 422 and characterized by a torus-like concave interior geometry at the lower chamber surfaces 37 adjacent the lower opening 524. More specifically, the body interior surface 126 progresses from an essentially cylindrical surface adjacent the body axial bore 422 and transitions through a hemi-concave surface tracing out approximately 45 degrees and smoothly inflects to a partially-concave surface tracing out approximately degrees adjacent the body lower opening 524.

The bushing 40/140 is characterized by an exterior surface 555 that assumes a generally cylindrical geometry adjacent the upper end 47 and smoothly transitions to a torus-like concave geometry along the lower exterior surface portion 555 and adjacent the lower end portion 546. As the bushing 40/140 is urged downward through the polyaxial bone fixation assembly 100 and the lower exterior surface portion 555 bears against the lower chamber surfaces 37 of the body 20/120, the interior cavity 551 is crush locked around the head of the bone anchor as the flexible arms 545 are drawn together and the position and angulation of the bone anchor is locked with respect to the body 20/120 and the polyaxial bone fixation assembly 100. The dark arrows show in FIGS. 16A and 16B illustrate a point of contact between the body 20/120 and the bushing 40/140 when in the locked state.

Thus, as described above, in the first and second embodiments of FIGS. 1 and 2, the interaction of the bone anchor, bushing and body have specifically designed sections thereof that come into contact to secure the bone anchor within the bushing, as described in FIGS. 5-16. In FIGS. 17 and 18, the interaction of the bone anchor and the bushing involves the head of the bone anchor deflecting the bushing as the head is inserted into the bushing. The arms of the bushing deflect outwardly as the head is inserted and then inwardly as the head is received within the bushing to secure the head therein.

Referring now to FIGS. 17A and 18A, there is illustrated a third embodiment of bone anchor or bone fixation assembly 1700 that generally includes a bone anchor 10 (e.g., a bone screw), a body 1720, a bushing 1740, and a locking cap 92. In the implementation of FIG. 17A, the bushing 1740 has a size and configuration to create an interference fit between the bushing 1740 and the bone anchor 10, whereas in the implementation of FIGS. 1A-1D the bushing 40 include a cavity 51 that is shaped and sized to engage and secure the head 14 when pushing is locked into place. As in the above, the anchor assembly 1700 enables in-situ assembly of the bone anchor 10 to the body 1720 of the anchor assembly 1700 such that the bone anchor 10 may be secured to a patients vertebra prior to being received within the body 1720. Aspects of the anchor assembly 1700 that are similar to the anchor assembly 100 are not repeated below.

The bushing 1740 may be movably positionable within the body 20 between a first (unloaded/unlocked) position where the bone anchor 10 can be connected to or unconnected from the bushing 1740, and a second (loaded/locked) position where the bone anchor 10 is locked with respect to the bushing 1740. The bushing 1740 defines slots, as in FIGS. 1 and 2, that define a plurality of flexible arms 1745 that pivot about a point 1753 (FIG. 18A). The slots may extend from the lower end 1746, the upper end 1747 or both ends 1746, 1747.

To interconnect or attach the bone anchor 10 to the body 1720, the body 1720 may be provided with the bushing 1740 pre-assembled and in the loading position, in which a lower tooth 1741*a* of an upper portion of the bushing 1740 engages a tooth 1741*c* of the body in the locking mechanism 1738. The head 14 of the bone anchor 10 is inserted into the lower opening 1724 of the body 1720 and into the interior cavity 1751 of the bushing 1740. As the head 14 is further inserted into the interior cavity 1751 of the bushing 1740 such that the flexible arms 1745 initially pivot outwardly about the point 1753 and then back inwardly until it the head 14 engages the interior surfaces of flexible arms 1745 that pivot about the point 1753 of the bushing 1740 (see FIG. 18A). Thus, the head 14 is "clicked-in" to the bushing 40 as the flexible arms 45 retain the head 14 within the cavity 1751.

After the head 14 of the bone anchor 10 is fully inserted into the cavity 1751 of the bushing 1740, the bushing 1740 is moved down into the lower chamber of the body 1720 to prevent the head 14 of the bone anchor 10 from becoming dislodged from bushing 1740. The downward movement causes the upper portion of the bushing 1740 to be retained within the body 1720 by the interaction of the tooth 1741*b* engaging the tooth 1741*c* of the body 1720. When the bone anchor 10 is in the locked position the head 14 is able to rotate polyaxially within the cavity 1751, and thus about the body 20. As illustrated, the bushing 40 of the first implementation, provides for approximately 25° of angulation in any direction with respect to the longitudinal axis 1732. As illustrated, the neck portion 16 acts as a stop when the neck portion 16 contacts the lower and of the bushing 1740.

Referring to FIGS. 17B and 18B, there is illustrated a fourth embodiment of a bone anchor or bone fixation assembly 1800 that generally includes a bone anchor 10 (e.g., a bone screw), a body 1820, a bushing 1840, and a locking cap 92. In the implementation of FIG. 17B, the bushing 1840 has a size and configuration to create an interference fit between the bushing 1840 and the bone anchor 10, whereas in the implementation of FIGS. 2A-2E the bushing 140 include a cavity 151 that is shaped and sized to engage and secure the head 14 when pushing is locked into place. As shown in FIGS. 17B and 18B, the bushing 1840 is sized and configured such that it may be inserted into the body 1820 through the upper opening, but is prevented from exiting through the lower opening.

Referring again to FIGS. 17B and 18B, once the bushing 1840 is placed and assembled into the body 1820, the bushing 1840 may be retainable within the body 1820 by a saddle 1869. For example, after the bushing 1840 is positioned, the saddle 1869 may be inserted into the upper opening 1823 such that a lower surface 1873 of the saddle 1869 contacts an upper surface 1872 of the bushing 1840. As such, the bushing 1840 is retained within the lower chamber 1836 of the body 1820.

The bushing 1840 is movably positionable within the body 1820 between a first position where the bone anchor 10 can be connected to or unconnected from the bushing 1840, and a second position where the bushing 1840 is locked with respect to the bone anchor 10. The lower end portion 1836 of the bushing 1840 preferably includes an interior cavity 1851 for receiving and securing the head 14 of the bone anchor 10 so that the bone anchor 10 can rotate polyaxially through a range of angles with respect to the bushing 1840 and hence with respect to the body 1820 when in an unlocked or loading/unloading position.

To interconnect or attach the bone anchor 10 to the body 1820, the body 1820 may be provided with the bushing 1840 pre-assembled and in the loading position, in which a lower tooth 1841a of the saddle 1869 engages a tooth 1841c of the body in the locking mechanism 1838. The lower surface 1873 of the saddle 1869 contacts the upper surface 1872 of the bushing 1840. The head 14 of the bone anchor 10 is inserted into the lower opening 1824 of the body 1820 and into the interior cavity 1851 of the bushing 1840. As shown in FIG. 18B, the head 14 is further inserted into the interior cavity 1851 of the bushing 1840, the flexible arms 1845 initially pivot outwardly about the point 1853 and then back inwardly until it the head 14 engages the interior surfaces of flexible arms 1845 that pivot about a point 1853 of the bushing 1840. Thus, the head 14 is "snapped-in" to the bushing 1840 as the flexible arms 1845 frictionally retain the head 14 within the cavity 1851.

When the bone anchor 10 is in the locked position the head 14 is rotatable within the cavity 1851. The bushing 140 of the fourth implementation, provides for approximately 41° of angulation in each direction with respect to the longitudinal axis 32, as both the head 14 and the bushing 1841 are rotatable within the lower chamber 1836 of the body 1820.

While the foregoing description and drawings represent the preferred embodiment of the present disclosure, it will be understood that various additions, modifications, combinations and/or substitutions may be made therein without departing from the spirit and scope of the present disclosure as defined in the accompanying claims. In particular, it will be clear to those skilled in the art that the present disclosure may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the disclosure, which are particularly adapted to specific environments and operative requirements without departing from the principles of the present disclosure. In addition, features described herein may be used singularly or in combination with other features. The presently disclosed embodiments are, therefore, to be considered in all respects as illustrative and not restrictive, the scope of the disclosure being indicated by the appended claims and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present disclosure, as defined by the appended claims.

The invention claimed is:
1. A bone anchor assembly comprising:
a bone anchor including a head and an elongated body portion for engaging a bone;
a body defining a cylindrical-shaped structure with a bore extending longitudinally therethrough, a distal end of the body including a distal opening larger than the head of the bone anchor such that the bone anchor can be received into the body via the distal opening;
a bushing received within the bore extending through the body, the bushing including a rod receiving channel extending through a sidewall of the bushing, the rod receiving channel sized and configured to receive a spinal rod extending laterally through the bushing, the bushing including a distal opening for receiving the head of the bone anchor;
a locking cap movable between a locked configuration and an unlocked configuration to independently fix the bone anchor and a spinal rod within the bushing, a distal end of the locking cap including a tapered distal edge defining an angled tapered surface corresponding to a tapered proximal edge on a proximal end of the bushing; and
a setscrew received within a threaded opening of the locking cap, a distal end of the setscrew extending beyond the distal end of the locking cap, the distal end of the setscrew defining a maximum diameter of the set screw, the maximum diameter greater than a diameter of the threaded opening,
wherein an inner surface of the bore extending through the body includes a first engagement feature for releasably coupling the body to the locking cap and a second engagement feature located between the first engagement feature and the distal opening for releasably coupling the body to the bushing,
wherein the second engagement feature engages a corresponding ratchet tooth extending from an outer surface of the bushing to retain the bushing within the bore of the body, where the second engagement feature is separated from the first engagement feature and spaced longitudinally along the inner surface of the bore from the first engagement feature, and where a portion of the bore between the first and second engagement features includes an increased diameter portion having a diameter greater than a diameter of the bore at the first and second engagement portions.
2. The bone anchor assembly of claim 1, wherein the locking cap comprises a threaded ring threadably coupled to a thread provided on the bore extending through the body to fix a longitudinal position of the bushing within the bore, where the tapered distal edge of the locking cap is provided on the threaded ring,
wherein the setscrew threadably couples to the opening in the threaded ring to retain a spinal rod within the rod receiving channel of the bushing, wherein the maximum diameter of the distal end of the setscrew prevents the distal end of the setscrew from being received within the threaded opening of the threaded ring.

3. The bone anchor assembly of claim 2, wherein the bushing includes a proximally extending sidewall portion extending from each side of the rod receiving channel, the proximally extending sidewall portions sized to extend above a spinal rod received with the rod receiving channel and engage the threaded ring separate from engagement between the setscrew and the spinal rod.

4. The bone anchor assembly of claim 3, wherein the rod receiving channel forms a U-shaped channel with the proximally extending sidewall portions extending from opposing sides of the rod receiving channel,
wherein, in the locked configuration, the setscrew extends beyond the distal opening of the locking cap and between the first and second sidewall portions, into contact with a spinal rod located within the rod receiving channel.

5. The bone anchor assembly of claim 2, wherein threaded engagement between the threaded ring and the body moves the threaded ring downward longitudinally within the body and into contact with the bushing.

6. The bone anchor assembly of claim 5, wherein continued threaded engagement and downward movement of the threaded ring brings a distal end of the threaded ring of the locking cap into contact with the proximal end of the bushing and results in a corresponding downward movement of the bushing within the body, thereby causing the bushing to engage the head of the bone anchor.

7. The bone anchor assembly of claim 6, wherein the downward movement of the bushing causes an end portion of the bushing to contact the body and urge radially inward and engage the head of the bone anchor, thereby fixing the position of the bone anchor with respect to the body
wherein a portion of the head of the bone anchor defining a maximum diameter of the head is retained within the bushing in the locked configuration.

8. The bone anchor assembly of claim 6, wherein the tapered distal edge of the locking cap is provided on the threaded ring, the tapered distal edge defining the angled tapered surface having an increasing taper between a proximal end and the distal end of the threaded ring,
wherein the tapered proximal edge of the bushing defines an angled tapered surface having an increasing taper between the proximal end and a distal end of the bushing.

9. The bone anchor assembly of claim 2, wherein, in the locked configuration, the setscrew extends through the central opening of the threaded ring and into the rod receiving channel of the bushing, fixing a position of a spinal rod extending through the rod receiving channel.

10. The bone anchor assembly of claim 2, further including:
a spinal rod sized and configured to extend laterally through the rod receiving channel of the bushing;
wherein the rod receiving channel of the bushing defines a generally U-shaped channel having a depth greater than a diameter of the spinal rod,
wherein the setscrew extends through the central opening of the threaded ring and into the rod receiving channel of the bushing fixing the spinal rod within the rod receiving channel.

11. The bone anchor assembly of claim 1, wherein the body includes a proximal opening at a proximal end of the body, the bore of the body extending between the proximal and distal openings,
wherein the proximal opening has a first diameter (D1) and the distal opening has a second diameter (D2), where the first diameter (D1) is larger than the second diameter (D2).

12. The bone anchor assembly of claim 1, wherein the body further includes a rod receiving channel extending through a side wall of the body sized and configured to receive a spinal rod extending laterally therethrough, the rod receiving channel of the body being aligned with the rod receiving channel of the bushing.

13. The bone anchor assembly of claim 1, wherein the bushing is frictionally retained within the bore extending through the body.

14. The bone anchor assembly of claim 1, wherein the first engagement feature includes at least one of thread, a cam-lock, a quarter lock, a clamp, a lug, and a bayonet.

15. The bone anchor assembly of claim 1,
wherein engagement between the second engagement feature and the ratchet tooth causes the bushing to align within the bore extending through the body at a predetermined orientation.

16. The bone anchor assembly of claim 1, wherein the bushing includes a bore extending longitudinally between a proximal opening and the distal opening,
wherein a portion of the bore extending through the bushing proximate the distal opening defines a curved surface having a shape corresponding to a curved surface of the head of the bone anchor to facilitate polyaxial rotation of the bone anchor when retained within the bushing.

17. The bone anchor assembly of claim 1, wherein an inner surface of the bore extending through the body includes a shoulder provided around a circumference of the inner surface,
wherein the shoulder engages a corresponding shoulder extending circumferentially from an outer surface of the bushing to limit downward movement of the bushing within the bore.

18. A bone anchor assembly comprising:
a bone anchor including a head and an elongated body portion for engaging a bone;
a body defining a cylindrical-shaped structure with a bore extending longitudinally therethrough, a distal end of the body including a distal opening larger than the head of the bone anchor such that the bone anchor can be received into the body via the distal opening;
a bushing received within the bore extending through the body, the bushing including U-shaped rod receiving channel extending through a sidewall of the bushing, the rod receiving channel sized and configured to receive a spinal rod extending laterally through the bushing, the bushing including a distal opening for receiving the head of the bone anchor; and
a locking cap including a threaded ring and a setscrew received within a central opening of the threaded ring, a distal end of the setscrew projecting beyond the central opening of the threaded ring and having a diameter greater than a diameter of the central opening of the threaded ring, the threaded ring received within the bore extending through the body to fix a longitudinal position of the bushing within the bore, a distal end of the threaded ring including a tapered distal edge defining an angled tapered surface corresponding to a tapered proximal edge on a proximal end of the bushing, and a portion of the setscrew extending through the central opening of the threaded ring and into the rod receiving channel to fix a position of a spinal rod within the rod receiving channel, wherein an inner surface of the bore extending through the body includes a threaded portion for releasably coupling the body to the threaded ring of the locking cap and a shoulder located between the threaded portion and the distal opening for releasably coupling the body to the bushing, wherein the shoulder engages a corresponding ratchet tooth extending from an outer surface of the bushing to retain the bushing within the bore of the body, where the shoulder is separated from the threaded portion and spaced longitudinally along the inner surface of the bore from the threaded portion, and where a portion of the bore between the threaded portion and the shoulder includes an increased diameter portion having a diameter greater than a diameter of the bore at the threaded portion and the shoulder.

19. A method of assembling a bone anchor assembly including:

placing a bone anchor into bone, the bone anchor including a head and an elongated body portion for engaging a bone, connecting a main housing of the bone anchor assembly to the head of the bone anchor, the main housing comprising:

a body member defining a cylindrical-shaped structure with a bore extending longitudinally therethrough, an inner surface of the bore including a threaded portion and a shoulder located between the threaded portion and an opening at a distal end of the body member, the threaded portion separated from the shoulder and spaced longitudinally along the inner surface of the bore from the shoulder, where a portion of the bore between the threaded portion and the shoulder includes an increased diameter portion having a diameter greater than a diameter of the bore at the threaded portion and the shoulder, the distal opening larger than the head of the bone anchor, the bone anchor received within the body member via the distal opening; and a bushing received within the bore extending through the body member, the bushing including a U-shaped rod receiving channel extending through a sidewall of the bushing, the rod receiving channel sized and configured to receive a spinal rod extending laterally through the bushing, the bushing including a distal opening for receiving the head of the bone anchor, the bushing including ratchet tooth extending from an outer surface of the bushing for retaining the bushing within the bore of body;

positioning the main housing at a desired angle with respect to the bone anchor;

placing a spinal rod within the rod receiving channel of the bushing;

attaching a locking cap to the main housing, the locking cap movable between a locked configuration and an unlocked configuration to independently fix the bone anchor and the spinal rod within the bushing, the locking cap including a threaded ring and a setscrew received within a threaded central opening of the threaded ring, the threaded ring received within the bore extending through the body member to fix a longitudinal position of the bushing within the bore, a distal end of the threaded ring including a tapered distal edge defining an angled tapered surface corresponding to a tapered proximal edge on a proximal end of the bushing, and a distal end of the setscrew projecting beyond the threaded central opening of the threaded ring and having a diameter greater than a diameter of the threaded central opening, the distal end of the setscrew defining a maximum diameter of the set screw, the distal end of the setscrew extending into the rod receiving channel to fix a position of a spinal rod within the rod receiving channel;

deploying the locking cap to independently lock a position of the main housing relative to the bone anchor and the spinal rod;

deploying the locking cap to lock a position of the spinal rod relative to the main housing.

20. The method of claim 19, wherein attaching the locking cap to the main housing comprises threadably coupling an outside thread provided on the threaded ring with a corresponding thread provided on the bore extending through the body member, wherein deploying the locking cap to independently lock a position of the main housing relative to the bone anchor comprises first providing continued threaded engagement between the threaded ring and the body member to move the threaded ring downward longitudinally within the body member and into contact with the bushing, contact with the busing resulting in a corresponding downward movement of the bushing to engage the head of the bone anchor and fix the position of the bone anchor with respect to the body member, followed by deploying the locking cap to lock a position of the spinal rod relative to the main housing by providing continued threading engagement between the setscrew and the threaded central opening of the threaded ring to move the setscrew downward longitudinally into the rod receiving channel to retain the spinal rod within the rod receiving channel of the bushing.

\* \* \* \* \*